(12) United States Patent
Lavi et al.

(10) Patent No.: US 12,079,994 B2
(45) Date of Patent: Sep. 3, 2024

(54) METHODS AND APPARATUS FOR ANGIOGRAPHIC IMAGE SELECTION

(71) Applicant: CathWorks Ltd., Kfar Saba (IL)

(72) Inventors: Guy Lavi, Moshav Mishmeret (IL); Ifat Lavi, Moshav Mishmeret (IL); Michael E. Juran, Kfar Saba (IL)

(73) Assignee: CathWorks Ltd., Kfar Saba (IL)

( * ) Notice: Subject to any disclaimer, the term of this patent is extended or adjusted under 35 U.S.C. 154(b) by 253 days.

(21) Appl. No.: 17/599,962

(22) PCT Filed: Mar. 26, 2020

(86) PCT No.: PCT/IB2020/052879
§ 371 (c)(1),
(2) Date: Sep. 29, 2021

(87) PCT Pub. No.: WO2020/201942
PCT Pub. Date: Oct. 8, 2020

(65) Prior Publication Data
US 2022/0172368 A1 Jun. 2, 2022

Related U.S. Application Data

(60) Provisional application No. 62/827,261, filed on Apr. 1, 2019.

(51) Int. Cl.
*G06T 7/00* (2017.01)
*G06T 7/60* (2017.01)
(Continued)

(52) U.S. Cl.
CPC .............. *G06T 7/0016* (2013.01); *G06T 7/60* (2013.01); *G06T 7/70* (2017.01); *G06V 10/22* (2022.01);
(Continued)

(58) Field of Classification Search
CPC ........... G06T 7/0016; G06T 7/60; G06T 7/70; G06T 2207/10116; G06T 2207/30048;
(Continued)

(56) References Cited

U.S. PATENT DOCUMENTS 5,150,292 A 9/1992 Hoffmann et al.
5,638,823 A 6/1997 Akay et al.
(Continued)

FOREIGN PATENT DOCUMENTS

AU 2010298333 1/2012
CN 104282009 1/2015
(Continued)

OTHER PUBLICATIONS

Wang et al, Optimal Viewing Angle Determination for Multiple Vessel Segments in Coronary Angiographic Image, IEEE Transactions on Nuclear Science, vol. 61, No. 3, pp. 1290-1303, Jun. 2014.*
(Continued)

*Primary Examiner* — Ping Y Hsieh
*Assistant Examiner* — Xiao Liu
(74) *Attorney, Agent, or Firm* — Knobbe, Martens, Olson & Bear, LLP

(57) ABSTRACT

A method and apparatus for selecting (i) an imaging angle with minimized foreshortening and/or overlap of a target region from an existing angiographic image and/or (ii) selecting an imaging angle for new images so that foreshortening and/or overlap are minimized. A viewing angle cost function is determined that defines optimal viewing angles at least with respect to minimizing foreshortening of the target region. Using the cost function, an image may be selected from among a set of images, which potentially does not match the optimal imaging angle due to the optimal imaging angle having a high cost as a result of overlapping vascular features. The selected image may have an imaging angle that (Continued)

corresponds to a lower cost due to less overlap compared to the optimal imaging angle.

33 Claims, 16 Drawing Sheets

(51) Int. Cl.
  *G06T 7/70*      (2017.01)
  *G06V 10/22*     (2022.01)
  *G16H 30/40*     (2018.01)

(52) U.S. Cl.
  CPC .... *G16H 30/40* (2018.01); *G06T 2207/10116* (2013.01); *G06T 2207/30048* (2013.01); *G06T 2207/30096* (2013.01); *G06T 2207/30104* (2013.01)

(58) Field of Classification Search
  CPC ........... G06T 2207/30096; G06T 2207/30104; G06V 10/22; G16H 30/40; G16H 30/20; G16H 50/50; A61B 6/504
  See application file for complete search history.

(56) References Cited

U.S. PATENT DOCUMENTS

| | | | |
|---|---|---|---|
| 6,047,080 | A  | 4/2000  | Chen et al. |
| 6,236,878 | B1 | 5/2001  | Taylor et al. |
| 6,842,638 | B1 | 1/2005  | Suri et al. |
| 7,113,623 | B2 | 9/2006  | Chen et al. |
| 7,339,585 | B2 | 3/2008  | Verstraelen et al. |
| 7,369,691 | B2 | 5/2008  | Kondo et al. |
| 7,574,026 | B2 | 8/2009  | Rasche et al. |
| 7,657,299 | B2 | 2/2010  | Huizenga et al. |
| 7,693,315 | B2 | 4/2010  | Krishnan et al. |
| 7,738,626 | B2 | 6/2010  | Weese et al. |
| 7,808,503 | B2 | 10/2010 | Duluk, Jr. et al. |
| 7,864,997 | B2 | 1/2011  | Aben |
| 7,912,260 | B2 | 3/2011  | Breeuwer et al. |
| 7,970,187 | B2 | 6/2011  | Puts et al. |
| 8,073,224 | B2 | 12/2011 | Strobel et al. |
| 8,086,000 | B2 | 12/2011 | Weijers et al. |
| 8,090,164 | B2 | 1/2012  | Bullitt et al. |
| 8,155,411 | B2 | 4/2012  | Hof et al. |
| 8,298,147 | B2 | 10/2012 | Huennekens et al. |
| 8,311,748 | B2 | 11/2012 | Taylor et al. |
| 8,311,750 | B2 | 11/2012 | Taylor |
| 8,315,812 | B2 | 11/2012 | Taylor |
| 8,321,150 | B2 | 11/2012 | Taylor |
| 8,331,314 | B2 | 12/2012 | Quiang et al. |
| 8,496,594 | B2 | 7/2013  | Taylor et al. |
| 8,523,779 | B2 | 9/2013  | Taylor et al. |
| 8,548,778 | B1 | 10/2013 | Hart et al. |
| 8,554,490 | B2 | 10/2013 | Tang et al. |
| 8,560,968 | B1 | 10/2013 | Nair |
| 8,768,669 | B1 | 7/2014  | Hart et al. |
| 8,771,195 | B2 | 7/2014  | Kim et al. |
| 8,787,641 | B2 | 7/2014  | Hof et al. |
| 8,812,246 | B2 | 8/2014  | Taylor |
| 8,824,752 | B1 | 9/2014  | Fonte et al. |
| 8,837,860 | B1 | 9/2014  | Grady et al. |
| 8,861,820 | B2 | 10/2014 | Fonte et al. |
| 8,917,925 | B1 | 12/2014 | Grady et al. |
| 8,970,578 | B2 | 3/2015  | Voros et al. |
| 9,008,405 | B2 | 4/2015  | Fonte et al. |
| 9,042,613 | B2 | 5/2015  | Spilker et al. |
| 9,070,214 | B1 | 6/2015  | Grady et al. |
| 9,078,564 | B2 | 7/2015  | Taylor |
| 9,087,147 | B1 | 7/2015  | Fonte |
| 9,129,418 | B2 | 9/2015  | Schormans et al. |
| 9,138,147 | B2 | 9/2015  | Schmitt et al. |
| 9,153,047 | B1 | 10/2015 | Grady et al. |
| 9,189,600 | B2 | 11/2015 | Spilker et al. |
| 9,256,936 | B2 | 2/2016  | Jacobs et al. |
| 9,314,584 | B1 | 4/2016  | Riley et al. |
| 9,375,191 | B2 | 6/2016  | Verstraelen et al. |
| 9,406,141 | B2 | 8/2016  | Kelm et al. |
| 9,430,827 | B2 | 8/2016  | Kelm et al. |
| 9,466,117 | B2 | 10/2016 | Habets et al. |
| 9,471,999 | B2 | 10/2016 | Ishii et al. |
| 9,572,495 | B2 | 2/2017  | Schmitt et al. |
| 9,576,360 | B2 | 2/2017  | Schormans et al. |
| 9,613,186 | B2 | 4/2017  | Fonte |
| 9,615,755 | B2 | 4/2017  | Riley et al. |
| 9,633,454 | B2 | 4/2017  | Lauritsch et al. |
| 9,646,361 | B2 | 5/2017  | Koo et al. |
| 9,743,835 | B2 | 8/2017  | Taylor |
| 9,754,082 | B2 | 9/2017  | Taylor et al. |
| 9,786,068 | B2 | 10/2017 | Ishii et al. |
| 9,814,433 | B2 | 11/2017 | Benishti et al. |
| 9,858,387 | B2 | 1/2018  | Lavi et al. |
| 9,870,634 | B2 | 1/2018  | Grady et al. |
| 9,888,896 | B2 | 2/2018  | Lauritsch et al. |
| 9,934,566 | B2 | 4/2018  | Sun et al. |
| 9,940,736 | B2 | 4/2018  | Ishii et al. |
| 9,943,233 | B2 | 4/2018  | Lavi et al. |
| 9,965,873 | B2 | 5/2018  | Grady et al. |
| 9,968,256 | B2 | 5/2018  | Taokowsky et al. |
| 9,977,869 | B2 | 5/2018  | Lavi et al. |
| 9,999,361 | B2 | 6/2018  | Sharma et al. |
| 10,141,074 | B2 | 11/2018 | Lavi et al. |
| 10,143,390 | B2 | 12/2018 | Ledoux et al. |
| 10,159,529 | B2 | 12/2018 | Taylor |
| 10,176,575 | B2 | 1/2019  | Isgum et al. |
| 10,210,956 | B2 | 2/2019  | Lavi et al. |
| 10,219,704 | B2 | 3/2019  | Lavi et al. |
| 10,229,516 | B2 | 3/2019  | Aben et al. |
| 10,235,796 | B2 | 3/2019  | Aben et al. |
| 10,245,001 | B2 | 4/2019  | Redel et al. |
| 10,342,442 | B2 | 7/2019  | Hattangadi et al. |
| 10,354,744 | B2 | 7/2019  | Sharma et al. |
| 10,360,674 | B2 | 7/2019  | Contini et al. |
| 10,363,018 | B2 | 7/2019  | Fukuda et al. |
| 10,373,700 | B2 | 8/2019  | Sharma et al. |
| 10,376,165 | B2 | 8/2019  | Lavi et al. |
| 10,395,366 | B2 | 8/2019  | Isgum et al. |
| 10,395,774 | B2 | 8/2019  | Lavi et al. |
| 10,420,610 | B2 | 9/2019  | Bai et al. |
| 10,424,063 | B2 | 9/2019  | Lavi et al. |
| 10,441,235 | B2 | 10/2019 | Lavi et al. |
| 10,441,239 | B2 | 10/2019 | Abe |
| 10,456,094 | B2 | 10/2019 | Fonte et al. |
| 10,463,336 | B2 | 11/2019 | Itu et al. |
| 10,470,730 | B2 | 11/2019 | Benishti et al. |
| 10,559,388 | B2 | 2/2020  | Lavi et al. |
| 10,580,526 | B2 | 3/2020  | Ma et al. |
| 10,595,807 | B2 | 3/2020  | Lavi et al. |
| 10,631,737 | B2 | 4/2020  | Lavi et al. |
| 10,636,146 | B2 | 4/2020  | Zhong et al. |
| 10,650,522 | B2 | 5/2020  | Hoi et al. |
| 10,682,180 | B2 | 6/2020  | Taylor |
| 10,699,407 | B2 | 6/2020  | Isgum et al. |
| 10,733,792 | B2 | 8/2020  | Aben et al. |
| 10,740,961 | B2 | 8/2020  | Reiber et al. |
| 10,748,285 | B2 | 8/2020  | Igarashi et al. |
| 10,758,200 | B2 | 9/2020  | Passerini et al. |
| 10,776,988 | B2 | 9/2020  | Grady et al. |
| 10,803,994 | B2 | 10/2020 | Lavi et al. |
| 10,803,995 | B2 | 10/2020 | Sharma et al. |
| 10,828,109 | B2 | 11/2020 | Redel |
| 10,854,329 | B2 | 12/2020 | Mohr et al. |
| 10,964,017 | B2 | 3/2021  | Pack et al. |
| 10,964,071 | B2 | 3/2021  | Grady et al. |
| 11,004,198 | B2 | 5/2021  | Isgum et al. |
| 11,017,531 | B2 | 5/2021  | Harish et al. |
| 11,031,136 | B2 | 6/2021  | Grass et al. |
| 11,055,845 | B2 | 7/2021  | Nickisch et al. |
| 11,076,770 | B2 | 8/2021  | Lavi et al. |
| 11,081,237 | B2 | 8/2021  | Lavi et al. |
| 11,083,377 | B2 | 8/2021  | Bouwman et al. |
| 11,083,524 | B2 | 8/2021  | Taylor |
| 11,087,884 | B2 | 8/2021  | Sankaran et al. |
| 11,090,118 | B2 | 8/2021  | Taylor |

(56) References Cited

U.S. PATENT DOCUMENTS

| | | |
|---|---|---|
| 11,116,575 B2 | 9/2021 | Taylor |
| 11,127,503 B2 | 9/2021 | Rabbat et al. |
| 11,138,733 B2 | 10/2021 | Lavi et al. |
| 11,141,123 B2 | 10/2021 | Homann et al. |
| 11,160,524 B2 | 11/2021 | Lavi et al. |
| 11,179,043 B2 | 11/2021 | Haase et al. |
| 11,185,368 B2 | 11/2021 | Spilker et al. |
| 11,195,278 B2 | 12/2021 | Nickisch et al. |
| 11,202,612 B2 | 12/2021 | Sakaguchi |
| 11,216,944 B2 | 1/2022 | Reiber et al. |
| 11,272,845 B2 | 3/2022 | Cheline et al. |
| 11,278,208 B2 | 3/2022 | Lavi et al. |
| 11,282,170 B2 | 3/2022 | Gauriau et al. |
| 11,288,811 B2 | 3/2022 | Tu et al. |
| 11,288,813 B2 | 3/2022 | Grady et al. |
| 11,295,864 B2 | 4/2022 | Benishti et al. |
| 11,298,187 B2 | 4/2022 | Taylor |
| 11,304,665 B2 | 4/2022 | Sharma et al. |
| 11,308,621 B2 | 4/2022 | Tu et al. |
| 11,328,824 B2 | 5/2022 | Fonte |
| 11,341,631 B2 | 5/2022 | Song et al. |
| 11,375,904 B2 | 7/2022 | Igarashi |
| 11,382,569 B2 | 7/2022 | Grady et al. |
| 11,389,130 B2 | 7/2022 | Itu et al. |
| 11,398,029 B2 | 7/2022 | Grady et al. |
| 11,406,337 B2 | 8/2022 | Lavi et al. |
| 11,406,339 B2 | 8/2022 | Mistretta et al. |
| 11,409,422 B2 | 8/2022 | Olivan Bescos et al. |
| 11,410,308 B2 | 8/2022 | Gulsun et al. |
| 11,423,532 B2 | 8/2022 | Takahashi et al. |
| 11,424,036 B2 | 8/2022 | Fonte et al. |
| 11,424,038 B2 | 8/2022 | Grady et al. |
| 11,443,428 B2 | 9/2022 | Petersen et al. |
| 11,445,923 B2 | 9/2022 | Tu et al. |
| 11,462,326 B2 | 10/2022 | Wang et al. |
| 11,462,329 B2 | 10/2022 | Rabbat et al. |
| 11,468,567 B2 | 10/2022 | Groth et al. |
| 11,482,339 B2 | 10/2022 | Koo et al. |
| 11,490,867 B2 | 11/2022 | Homann et al. |
| 11,501,485 B2 | 11/2022 | Grady et al. |
| 11,508,460 B2 | 11/2022 | Wang et al. |
| 11,510,587 B2 | 11/2022 | Kristanto et al. |
| 11,521,755 B2 | 12/2022 | Taylor et al. |
| 11,523,744 B2 | 12/2022 | Freiman et al. |
| 11,538,161 B2 | 12/2022 | Wang et al. |
| 11,540,931 B2 | 1/2023 | Grady et al. |
| 11,557,036 B2 | 1/2023 | Liao et al. |
| 11,557,069 B2 | 1/2023 | Senzig et al. |
| 11,559,274 B2 | 1/2023 | Auvray et al. |
| 11,564,746 B2 | 1/2023 | Spilker et al. |
| 11,564,748 B2 | 1/2023 | Thienphrapa et al. |
| 11,574,406 B2 | 2/2023 | Chen et al. |
| 11,576,621 B2 | 2/2023 | Sharma et al. |
| 11,576,626 B2 | 2/2023 | Fonte et al. |
| 11,576,637 B2 | 2/2023 | Schmitt et al. |
| 11,576,639 B2 | 2/2023 | Song et al. |
| 11,583,340 B2 | 2/2023 | Taylor |
| 11,589,924 B2 | 2/2023 | Passerini et al. |
| 11,599,996 B2 | 3/2023 | Isgum et al. |
| 11,607,189 B2 | 3/2023 | Tu et al. |
| 11,610,309 B2 | 3/2023 | Kweon et al. |
| 11,610,318 B2 | 3/2023 | Grady et al. |
| 11,615,894 B2 | 3/2023 | Lavi et al. |
| 11,617,620 B2 | 4/2023 | Tran et al. |
| 11,633,118 B2 | 4/2023 | Freiman et al. |
| 11,638,609 B2 | 5/2023 | Sankaran et al. |
| 11,642,171 B2 | 5/2023 | Jaquet et al. |
| 11,653,833 B2 | 5/2023 | Sanders et al. |
| 11,664,128 B2 | 5/2023 | Haase et al. |
| 11,688,502 B2 | 6/2023 | Anderson et al. |
| 11,690,518 B2 | 7/2023 | Haase et al. |
| 11,694,339 B2 | 7/2023 | Schormans et al. |
| 11,707,196 B2 | 7/2023 | Lavi et al. |
| 11,707,242 B2 | 7/2023 | Van Walsum et al. |
| 11,710,569 B2 | 7/2023 | Grass et al. |
| 11,728,037 B2 | 8/2023 | Lavi et al. |
| 11,741,602 B2 | 8/2023 | Reiber et al. |
| 11,744,472 B2 | 9/2023 | Zhao et al. |
| 11,744,544 B2 | 9/2023 | Sheehan et al. |
| 11,748,902 B2 | 9/2023 | Bai et al. |
| 11,756,195 B2 | 9/2023 | Kweon et al. |
| 11,769,254 B2 | 9/2023 | Song et al. |
| 11,776,149 B2 | 10/2023 | Wang et al. |
| 11,779,225 B2 | 10/2023 | Adiyoso |
| 11,779,233 B2 | 10/2023 | Huo et al. |
| 11,779,294 B2 | 10/2023 | Liu et al. |
| 11,786,202 B2 | 10/2023 | Yin et al. |
| 11,793,575 B2 | 10/2023 | Taylor |
| 11,803,966 B2 | 10/2023 | Denzinger et al. |
| 11,810,290 B2 | 11/2023 | Flohr et al. |
| 11,810,661 B2 | 11/2023 | Barley et al. |
| 11,816,836 B2 | 11/2023 | Isgum et al. |
| 11,816,837 B2 | 11/2023 | Lavi et al. |
| 11,826,106 B2 | 11/2023 | Hart et al. |
| 11,826,175 B2 | 11/2023 | Itu et al. |
| 11,847,547 B2 | 12/2023 | Wang et al. |
| 2003/0105401 A1 | 6/2003 | Jago et al. |
| 2004/0019264 A1 | 1/2004 | Suurmond et al. |
| 2004/0066958 A1 | 4/2004 | Chen et al. |
| 2005/0043614 A1 | 2/2005 | Huizenga et al. |
| 2005/0249327 A1 | 11/2005 | Wink et al. |
| 2005/0272992 A1 | 12/2005 | O'Donnell et al. |
| 2006/0036167 A1 | 2/2006 | Shina |
| 2006/0084862 A1 | 4/2006 | Suurmond et al. |
| 2007/0031019 A1 | 2/2007 | Lesage et al. |
| 2007/0167833 A1 | 7/2007 | Redel et al. |
| 2008/0020362 A1 | 1/2008 | Cotin et al. |
| 2008/0187199 A1 | 8/2008 | Gulsun et al. |
| 2008/0205722 A1 | 8/2008 | Schaefer et al. |
| 2009/0016483 A1 | 1/2009 | Kawasaki et al. |
| 2009/0171321 A1 | 7/2009 | Callaghan |
| 2009/0312648 A1 | 12/2009 | Zhang et al. |
| 2010/0010428 A1 | 1/2010 | Yu et al. |
| 2010/0017171 A1 | 1/2010 | Spilker et al. |
| 2010/0021025 A1 | 1/2010 | Hof et al. |
| 2010/0067760 A1 | 3/2010 | Zhang et al. |
| 2010/0125197 A1 | 5/2010 | Fishel |
| 2010/0160764 A1 | 6/2010 | Steinberg et al. |
| 2010/0220917 A1 | 9/2010 | Steinberg et al. |
| 2010/0296709 A1 | 11/2010 | Ostrovsky-Berman et al. |
| 2010/0298719 A1 | 11/2010 | Thrysoe et al. |
| 2011/0015530 A1 | 1/2011 | Misawa |
| 2011/0096907 A1 | 4/2011 | Mohamed |
| 2011/0134433 A1 | 6/2011 | Yamada |
| 2011/0135175 A1 | 6/2011 | Ostrovsky-Berman et al. |
| 2011/0142313 A1 | 6/2011 | Pack et al. |
| 2011/0182492 A1 | 7/2011 | Grass et al. |
| 2012/0014574 A1 | 1/2012 | Ferschel et al. |
| 2012/0041318 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0059249 A1 | 3/2012 | Verard et al. |
| 2012/0062841 A1 | 3/2012 | Stetson et al. |
| 2012/0072190 A1 | 3/2012 | Sharma et al. |
| 2012/0075284 A1 | 3/2012 | Rivers et al. |
| 2012/0150048 A1 | 6/2012 | Kang et al. |
| 2012/0177275 A1 | 7/2012 | Suri |
| 2012/0230565 A1 | 9/2012 | Steinberg et al. |
| 2012/0236032 A1 | 9/2012 | Arvidsson |
| 2012/0243761 A1 | 9/2012 | Senzig et al. |
| 2013/0060133 A1 | 3/2013 | Kassab et al. |
| 2013/0094745 A1 | 4/2013 | Sundar |
| 2013/0158476 A1 | 6/2013 | Olson |
| 2013/0226003 A1 | 8/2013 | Edic et al. |
| 2013/0229621 A1 | 9/2013 | Stetson et al. |
| 2013/0324842 A1 | 12/2013 | Mittal et al. |
| 2014/0005535 A1 | 1/2014 | Edic et al. |
| 2014/0086461 A1 | 3/2014 | Yao et al. |
| 2014/0094693 A1 | 4/2014 | Cohen et al. |
| 2014/0100451 A1 | 4/2014 | Tolkowsky et al. |
| 2014/0121513 A1 | 5/2014 | Tolkowsky et al. |

(56) References Cited

U.S. PATENT DOCUMENTS

| | | |
|---|---|---|
| 2014/0142398 A1 | 5/2014 | Patil et al. |
| 2014/0200867 A1 | 7/2014 | Lavi et al. |
| 2014/0303495 A1 | 10/2014 | Fonte et al. |
| 2014/0371578 A1* | 12/2014 | Auvray ............... A61B 6/503 600/424 |
| 2015/0201897 A1 | 7/2015 | Kyriakou |
| 2015/0250395 A1 | 9/2015 | Igarashi |
| 2015/0265162 A1 | 9/2015 | Lavi et al. |
| 2015/0302578 A1 | 10/2015 | Grady et al. |
| 2015/0335304 A1 | 11/2015 | Lavi et al. |
| 2015/0339847 A1 | 11/2015 | Benishti et al. |
| 2015/0342551 A1* | 12/2015 | Lavi ..................... G16H 50/50 600/407 |
| 2016/0007945 A1 | 1/2016 | Taylor |
| 2016/0022371 A1 | 1/2016 | Sauer et al. |
| 2016/0073928 A1 | 3/2016 | Soper et al. |
| 2016/0110866 A1 | 4/2016 | Taylor |
| 2016/0110867 A1 | 4/2016 | Taylor |
| 2016/0128661 A1 | 5/2016 | Taylor |
| 2016/0157802 A1 | 6/2016 | Anderson |
| 2016/0228000 A1 | 8/2016 | Spaide |
| 2016/0247279 A1* | 8/2016 | Lavi ..................... A61B 6/504 |
| 2016/0371456 A1 | 12/2016 | Taylor et al. |
| 2017/0018116 A1 | 1/2017 | Sun et al. |
| 2017/0039736 A1 | 2/2017 | Aben et al. |
| 2017/0224418 A1 | 8/2017 | Boettner et al. |
| 2017/0286628 A1 | 10/2017 | Shim |
| 2017/0325770 A1 | 11/2017 | Edic et al. |
| 2018/0032653 A1 | 2/2018 | Aben et al. |
| 2018/0075221 A1 | 3/2018 | Vergaro et al. |
| 2018/0089829 A1 | 3/2018 | Zhong et al. |
| 2018/0182096 A1 | 6/2018 | Grady et al. |
| 2018/0211386 A1 | 7/2018 | Ma et al. |
| 2018/0235561 A1 | 8/2018 | Lavi et al. |
| 2018/0243033 A1 | 8/2018 | Tran et al. |
| 2018/0268941 A1 | 9/2018 | Lavi et al. |
| 2018/0315193 A1 | 11/2018 | Paschalakis et al. |
| 2018/0330507 A1 | 11/2018 | Schormans et al. |
| 2018/0344173 A1 | 12/2018 | Tu et al. |
| 2018/0344174 A9 | 12/2018 | Schmitt et al. |
| 2019/0005737 A1 | 1/2019 | Auvray et al. |
| 2019/0019347 A1 | 1/2019 | Auvray et al. |
| 2019/0130578 A1 | 5/2019 | Gulsun et al. |
| 2019/0282199 A1 | 9/2019 | Merritt |
| 2019/0380593 A1 | 12/2019 | Bouwman et al. |
| 2020/0126229 A1 | 4/2020 | Lavi et al. |
| 2020/0138521 A1 | 5/2020 | Aben et al. |
| 2020/0160509 A1 | 5/2020 | Pack et al. |
| 2020/0222018 A1 | 7/2020 | van Walsum et al. |
| 2020/0265958 A1 | 8/2020 | Haase et al. |
| 2020/0337664 A1 | 10/2020 | Homann et al. |
| 2020/0394795 A1 | 12/2020 | Isgum et al. |
| 2021/0022617 A1 | 1/2021 | Zhao et al. |
| 2021/0035290 A1 | 2/2021 | Aben et al. |
| 2021/0244475 A1 | 8/2021 | Taylor |
| 2021/0259559 A1 | 8/2021 | Tu et al. |
| 2021/0267690 A1 | 9/2021 | Taylor |
| 2021/0272030 A1 | 9/2021 | Sankaran et al. |
| 2021/0275124 A1 | 9/2021 | Huo et al. |
| 2021/0280318 A1 | 9/2021 | Huo et al. |
| 2021/0282731 A1 | 9/2021 | Vaillant et al. |
| 2021/0282860 A1 | 9/2021 | Taylor |
| 2021/0290308 A1 | 9/2021 | Mihalef et al. |
| 2021/0298706 A1 | 9/2021 | Tu et al. |
| 2021/0298708 A1 | 9/2021 | Aben et al. |
| 2021/0334963 A1 | 10/2021 | Isgum et al. |
| 2021/0338088 A1 | 11/2021 | Bouwman et al. |
| 2021/0345889 A1 | 11/2021 | Tu et al. |
| 2021/0358634 A1 | 11/2021 | Sankaran et al. |
| 2021/0361176 A1 | 11/2021 | Huo et al. |
| 2021/0383539 A1 | 12/2021 | Haase et al. |
| 2021/0401400 A1 | 12/2021 | Sheehan et al. |
| 2022/0012876 A1 | 1/2022 | Sommer et al. |
| 2022/0015730 A1 | 1/2022 | Haase et al. |
| 2022/0036646 A1 | 2/2022 | Song et al. |
| 2022/0047236 A1 | 2/2022 | Lavi et al. |
| 2022/0054022 A1 | 2/2022 | Van Lavieren et al. |
| 2022/0079455 A1 | 3/2022 | Haase et al. |
| 2022/0079540 A1 | 3/2022 | Sankaran et al. |
| 2022/0079563 A1 | 3/2022 | Kemp |
| 2022/0087544 A1 | 3/2022 | Schmitt et al. |
| 2022/0092784 A1 | 3/2022 | Tu et al. |
| 2022/0110687 A1 | 4/2022 | Spilker et al. |
| 2022/0151580 A1 | 5/2022 | Itu et al. |
| 2022/0164953 A1 | 5/2022 | Gulsun et al. |
| 2022/0167938 A1 | 6/2022 | Grass et al. |
| 2022/0183655 A1 | 6/2022 | Huang et al. |
| 2022/0211280 A1 | 7/2022 | Lavi et al. |
| 2022/0211439 A1 | 7/2022 | Sankaran et al. |
| 2022/0230312 A1 | 7/2022 | Choi et al. |
| 2022/0233081 A1 | 7/2022 | Cheline et al. |
| 2022/0254028 A1 | 8/2022 | Liu et al. |
| 2022/0254131 A1 | 8/2022 | Lavi et al. |
| 2022/0261997 A1 | 8/2022 | Liu et al. |
| 2022/0262000 A1 | 8/2022 | Haase et al. |
| 2022/0273180 A1 | 9/2022 | Lavi et al. |
| 2022/0277447 A1 | 9/2022 | Wang et al. |
| 2022/0319004 A1 | 10/2022 | Bruch-el et al. |
| 2022/0319116 A1 | 10/2022 | Wang et al. |
| 2022/0335612 A1 | 10/2022 | Bruch-El et al. |
| 2022/0351369 A1 | 11/2022 | Haase et al. |
| 2022/0415510 A1 | 12/2022 | Wang et al. |
| 2023/0037338 A1 | 2/2023 | Wang et al. |
| 2023/0038364 A1 | 2/2023 | Bhowmick et al. |
| 2023/0084748 A1 | 3/2023 | Lavi et al. |
| 2023/0108647 A1 | 4/2023 | Tu et al. |
| 2023/0113721 A1 | 4/2023 | Kassel et al. |
| 2023/0148977 A1 | 5/2023 | Fonte et al. |
| 2023/0186472 A1 | 6/2023 | Kweon et al. |
| 2023/0196582 A1 | 6/2023 | Grady et al. |
| 2023/0197286 A1 | 6/2023 | Grady et al. |
| 2023/0230235 A1 | 7/2023 | Isgum et al. |
| 2023/0245301 A1 | 8/2023 | Wang et al. |
| 2023/0252628 A1 | 8/2023 | Haase et al. |
| 2023/0277247 A1 | 9/2023 | Taylor et al. |
| 2023/0282365 A1 | 9/2023 | Lavi et al. |
| 2023/0298176 A1 | 9/2023 | Choi et al. |
| 2023/0309943 A1 | 10/2023 | van Walsum et al. |
| 2023/0320789 A1 | 10/2023 | Bai et al. |
| 2023/0346236 A1 | 11/2023 | Lavi et al. |
| 2023/0352152 A1 | 11/2023 | Grady et al. |
| 2023/0355107 A1 | 11/2023 | Haase et al. |
| 2023/0360803 A1 | 11/2023 | Sankaran et al. |
| 2023/0386037 A1 | 11/2023 | Denzinger et al. |
| 2023/0404525 A1 | 12/2023 | Sheehan et al. |
| 2024/0029529 A1 | 1/2024 | Scalisi |

FOREIGN PATENT DOCUMENTS

| | | |
|---|---|---|
| EP | 1396274 | 3/2004 |
| EP | 2163272 | 3/2010 |
| EP | 2633815 A1 | 9/2013 |
| EP | 2779907 | 9/2014 |
| EP | 2873371 | 5/2015 |
| EP | 3125764 | 2/2017 |
| EP | 2633815 B1 | 6/2017 |
| EP | 3363350 | 8/2018 |
| EP | 3460688 | 3/2019 |
| EP | 3477551 | 5/2019 |
| EP | 3763285 | 1/2021 |
| EP | 3847956 | 7/2021 |
| EP | 2776960 | 9/2021 |
| EP | 3534372 | 9/2021 |
| EP | 3871184 | 9/2021 |
| EP | 3881758 | 9/2021 |
| EP | 3884868 | 9/2021 |
| EP | 3282380 | 11/2021 |
| EP | 3282381 | 11/2021 |
| EP | 3903672 | 11/2021 |
| EP | 3912139 | 11/2021 |
| EP | 3664026 | 2/2022 |
| EP | 3949860 | 2/2022 |
| EP | 3076854 | 4/2022 |
| EP | 3979259 | 4/2022 |

(56) References Cited

FOREIGN PATENT DOCUMENTS

| | | |
|---|---|---|
| EP | 3258446 | 5/2022 |
| EP | 4026143 | 7/2022 |
| EP | 4026491 | 7/2022 |
| EP | 4026492 | 7/2022 |
| EP | 4029438 | 7/2022 |
| EP | 3298959 | 9/2022 |
| EP | 3989828 | 11/2022 |
| EP | 3157411 | 12/2022 |
| EP | 3606437 | 12/2022 |
| EP | 4104765 | 12/2022 |
| EP | 4131150 | 2/2023 |
| EP | 4145391 | 3/2023 |
| EP | 3169237 | 4/2023 |
| EP | 3403582 | 6/2023 |
| EP | 3743883 | 6/2023 |
| EP | 3989832 | 8/2023 |
| EP | 3652747 | 9/2023 |
| EP | 4104766 | 9/2023 |
| EP | 3602485 | 10/2023 |
| EP | 4064181 | 11/2023 |
| EP | 3602487 | 12/2023 |
| JP | H08-131429 | 5/1996 |
| JP | 2003-508152 | 3/2003 |
| JP | 2003-514600 | 4/2003 |
| JP | 2004-243117 | 9/2004 |
| JP | 2007-502644 | 2/2007 |
| JP | 2007-325920 | 12/2007 |
| JP | 4177217 B2 | 11/2008 |
| JP | 2010-042247 | 2/2010 |
| JP | 2011-212314 | 10/2011 |
| JP | 2013-090799 | 5/2013 |
| JP | 2010-505493 | 7/2013 |
| JP | 2013-534154 | 9/2013 |
| JP | 2014-064915 | 4/2014 |
| JP | 2015-503416 | 2/2015 |
| JP | 2015-527901 | 9/2015 |
| NL | 2012324 | 8/2015 |
| WO | WO 2001/21057 | 3/2001 |
| WO | WO 2007/066249 | 6/2007 |
| WO | WO 2010/033971 | 3/2010 |
| WO | WO 2011/038044 | 3/2011 |
| WO | WO 2011/039685 | 4/2011 |
| WO | WO 2012/021037 | 2/2012 |
| WO | WO 2012/021307 | 2/2012 |
| WO | WO 2012/173697 | 12/2012 |
| WO | WO 2014/027692 | 2/2014 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/059706 | 4/2015 |
| WO | WO 2017/199246 | 11/2017 |
| WO | WO-2017199245 A1 * 11/2017 ............. A61B 34/10 | |
| WO | WO 2018/165478 | 9/2018 |
| WO | WO 2020/053099 | 3/2020 |
| WO | WO 2020/084101 | 4/2020 |
| WO | WO 2020/201942 | 10/2020 |
| WO | WO 2021/016071 | 1/2021 |
| WO | WO 2021/059165 | 4/2021 |
| WO | WO 2021/175039 | 9/2021 |
| WO | WO 2021/191909 | 9/2021 |

OTHER PUBLICATIONS

Wang et al, Global Optimization of Optimal Angiographic Viewing Angles for Coronary Arteries with Multiple Segments, 35th Annual International Conference of the IEEE EMBS, pp. 2640-2643, Osaka, Japan, Jul. 3-7, 2013.*
Chen et alll, 3-D reconstruction of coronary arterial tree to optimize angiographic visualization IEEE Trans. Medical Imaging, vol. 19, pp. 318-336 (Year: 2000).*
Abraham et al., "Alternative routes in road networks", ACM Journal of Experimental Algorithmics, Association of Computing Machinery, vol. 18(1):1.3:2-1.3:17 (2013).
Andriotis et al., "A new method of three-dimensional coronary artery reconstruction from X-Ray angiography: Validation against a virtual phantom and multislice computed tomography", Catheterization and Cardiovascular Interventions, vol. 71:28-43 (2008).
Barnea, "Model-based estimation of coronary vessel diameter in angiographic images", Proceedings of the 20th Annual International Conference of the IEEE Engineering in Medicine and Biology Society, vol. 20:513-516 (1998).
Barratt et al., "Reconstruction and quantification of the carotid artery bifurcation from 3-D ultrasound images", IEEE Transactions on Medical Imaging, vol. 23(5):567-583 (2004).
Barrett et al., "Interactive live-wire 1-3 boundary extraction", Medical Image Analysis, Oxford University Press, vol. 1(4):331-341 (1997).
Bullitt et al., "Determining malignancy of brain tumors by analysis of vessel shape", Medical Image Computing and Computer-Assisted Intervention, MICCAI 2004 Conference Proceedings, Lecture notes in Computer Science, LNCS, 3217:645-653.
Caiati et al., "New noninvasive method for coronary flow reserve assessment: Contrast-enhanced transthoracic second harmonic echo doppler", Circulation, vol. 99:771-778 (1999).
Caiati et al., "Detection, location, and severity assessment of left anterior descneding coronary artery stenoses by means of contrast-enhanced transthoracic harmonic echo dopper", European Heart Journal, vol. 30:1797-1806 (2009).
Chung, "Image segmentation methods for detecting blood vessels in angiography", 2006 9th International Conference on Control, Automation, Robotics and Vision, Singapore, pp. 1-6 (2006).
Dickie et al., "Live-vessel: interactive vascular image segmentation with simultaneous extraction of optimal medial and boundary paths", Technical Report TR 2009-23, School of Computing Science, Simon Fraser University, Burnaby, BC, Canada, Nov. 2009.
Frangi et al., "Multiscale vessel and enhancement filtering", Medical Image Computing and Computer-Assisted Intervention, MICCA '98 Lecture Notes in Computer Science, vol. 1496:130-137 (1998).
Fraz, "Blood vessel segmentation methodologies, in retinal images—a survey", Computer Methods and Programs in Biomedicine, vol. 108:407-433 (2012).
Fusejima, "Noninvasive measurement of coronary artery blood flow using combined two-dimensional and doppler echocardiography", JACC vol. 10(5):1024-1031 (1987).
Hawkes et al., "Validation of volume blood flow measurements using three-dimensional distance-concentration functions detived from digital X-Ray angiograms", Investigative Radiology, vol. 29(4):434-442 (1994).
Hoffmann et al., "Determination of instantaneous and average blood flow rates from digital angiograms of vessel phantoms using distance-density curves", Investigative Radiology, vol. 26(3):207-212 (1991).
Holdsworth et al., "Quantitative angiographic blood-flow measurement using pulsed intra-arterial injection", Medical Physics, vol. 26(10):2168-2175 (1999).
Huo et al., "Intraspecific scaling laws of vascular trees", J.R. Soc. Interface vol. 9:190-200 (2012).
Janssen et al., "New approaches for the assessment of vessel sizes in quantitative (cardio-)vascular X-ray analysis", Int J Cardiovasc Imaging vol. 26:259-271 (2010).
Jiang et al., "Vascular tree reconstruction by minimizing a physiological functional cost", 2010 IEEE Computer Society Conference on Computer Vision and Pattern Recognition—workshops, San Francisco, CA, pp. 178-185, doi: 10.1109/CVPRW.2010.5543593.
Kappetein et al, "Current percutaneous coronary intervention and coronary artery bypass grafting practices for three-vessel and left main coronary artery disease: Insights from the SYNTAX run-in phase", European Journal of Cardio-Thoracic Surgery, vol. 29:486-491 (2010).
Kass et al., "Snakes: active contour models", Int. J. Comput. Vis. vol. 1:321-331 (1987).
Kirkeeide, "Coronary obstructions, morphology and physiologic significance", Quantitative Coronary Arteriography, Chap. 11:229-244 (1991).
Lethen et al., "Validation of noninvasive assessment of coronary flow velocity reserve in the right coronary artery—A comparison of

(56) References Cited

OTHER PUBLICATIONS transthoracic echocardiographic results with intracoronary doppler flow wire measurements", European Heart Journal, vol. 24:1567-1575 (2003).
Li et al., "Minimization of region-scalable fitting energy for image segmentation", in IEEE Transactions on Image Processing, vol. 17(10):1940-1949 (2008).
Marchenko, et al., "Vascular editor: from angiographic images to 3D vascular models", Journal of Digital Imaging, vol. 23:386-398 (2010).
Meimoun et al., "Non-invasive assessment of coronary flow and coronary flow reserve by transthoracic doppler echocardiography: a magic tool for the real world", European Journal of Echocardiography, vol. 9:449-457 (2008).
Mercer-Rosa et al., "Illustration of the additional value of real-time 3-dimensional echocardiography to conventional transthoracic and transesophageal 2-dimensional echocardiography in imaging muscular ventricular septal defects: does this have any impact on individual patient treatment", Journal of the American Society of Echocardiography, vol. 19(12):1511-1519 (2006).
Molloi et al., "Quantification of fractional flow reserve using angiographic image data", World Congress on Medical Physics and Biomedical Engineering, Munich, Germany, Sep. 7-12, 2009.
Molloi et al., "Estimation of coronary artery hyperemic blood flow based on arterial lumen volume using angiographic images", Int J Cardiovasc Imaging, vol. 28:1-11 (2012).
Ng et al., "Novel QCA methodologies and angiographic scores", Int J Cardiovasc Imaging vol. 27:157-165 (2011).
Pellot et al, "A 3D reconstruction of vascular structures from two X-Ray angiograms using an adapted simulated annealing algorithm", IEEE Transactions of Medical Imaging, vol. 13(1):48-60 (1994).
Pinho et al., "Assessment and stenting of tracheal stenosis using deformable shape models", Medical Image Analysis, vol. 15(2):250-266 (2010).
Polytimi et al., "Close to transplant renal artery stenosis and percutaneous transluminal treatment", Journal of Transplantation, vol. 2011, 7 pages (2011).
Rabbat et al., "Interpreting results of coronary computed tomography angiography-derived fractional flow reserve in clinical practice", Journal of Cardiovascular Computed Tomography, vol. 11(5):1-6 (2017).
Sarwal et al., "3-D reconstruction of coronary arteries", Proceedings of the 16th Annual Intl. Conference of the IEEE Engineering in Medicine and Biology Society, Engineering Advances: New Opportunities for Biomedical Engineers, Nov. 3, 1994, pp. 504-505.
Sato et al., "A viewpoint determination system for stenosis diagnosis and quantification in coronary angiogrphic image acquisition", IEEE Transactions on Medical Imaging, vol. 17(1):121-137 (1998).
Seifalian et al., "A new algorithm for deriving pulsatile blood flow waveforms tested using simulated dynamic angiographic data", Neuroradiology, vol. 31:263-269 (1989).
Seifalian et al., "Blood flow measurements using 3D distance-concentration functions derived from digital x-ray angiograms", Cardiovascular Imaging, Chap. 33:425-442 (1996).
Seifalian et al., "Validation of a quantitative radiographic technique to estimate pulsatile blood flow waveforms using digital subtraction angiographic data", Journal of Biomedical Engineering, vol. 13(3):225-233 (1991).
Shang et al., "Vascular active contour for vessel tree segmentation", in IEEE Transactions on Biomedical Engineering, vol. 58(4):1023-1032 (2011).
Shpilfoygel et al., "Comparison of methods for instantaneous angiographic blood flow measurement", Medical Physics, vol. 26(6):862-871 (1999).
Sianos et al., "The SYNTAX score: an angiographic tool grading the complexity of coronary artery disease", Euro Intervention, vol. 1(2):219-227 (2005).
Siogkas et al., "Quantification of the effect of percutaneous coronary angioplasty on a stenosed right coronary artery", 2010 10th IEEE Intl. Conference on Information Technology and Applications in Biomedicine, Nov. 3-5, 210, pp. 1-4 (2010).
Slomka et al., "Fully automated wall motion and thickening scoring system for myocardial perfusion SPECT: Method development and validation in large population", Journal of Nuclear Cardiology, vol. 19(2):291-302 (2012).
Sprague et al., "Coronary x-ray angiographic reconstruction and image orientation", Medical Physics, vol. 33(3):707-718 (2006).
Sun et al., "Coronary CT angiography: current status and continuing challenges", The British Journal of Radiology, vol. 85:495-510 (2012).
Takarada et al., "An angiographic technique for coronary fractional flow reserve measurement: in vivo validation", International Journal of Cardiovascular Imaging, published online pp. 1-10, Aug. 31, 2012.
Termeer et al., "Visualization of myocardial perfusion derived from coronary anatomy", IEEE Transactions on Visualization and Computer Graphics, vol. 14(6):1595-1602 (2008).
Tomasello et al., "Quantitative coronary angiography in the interventional cardiology", Advances in the Diagnosis of Coronary Atherosclerosis, Chap. 14:255-272 (2011).
Tu et al., Assessment of obstruction length and optimal viewing angle from biplane X-ray angiograms, Int J Cardiovasc Imaging, vol. 26:5-17 (2010).
Tu et al., "In vivo assessment of optimal viewing angles from X-ray coronary angiography", EuroIntervention, vol. 7:112-120 (2011).
Tu et al., "In vivo assessment of bifurcation optimal viewing angles and bifurcation angles by three-dimentional (3D) quantitative coronary angiography", Int J Cardiovasc Imaging, published online Dec. 15, 2011, in 9 pages.
Tu et al., "The impact of acquisition angle differences on three-dimensional quantitative coronary angiography", Catheterization and Cardiovascular Interventions, vol. 78:214-222 (2011).
Tuinenburg et al., "Dedicated bifurcation analysis: basic principles", Int J Cardiovasc Imaging, vol. 27:167-174 (2001).
Voci et al., "Coronary flow: a new asset for the echo lab?", European Heart Journal, vol. 25:1867-1879 (2004).
Weickert et al., "A scheme for coherence-enhancing diffusion filtering with optimized rotation invariance", Computer Vision, Graphics, and Pattern Recognition Group, Technical Report, Computer Science Series, pp. 1-20 (2000).
Weickert, "Anisotropic diffusion in image processing", ECMI, published by Teubner Stuttgart, Germany, 181 pages (2008).
Weickert et al., "A scheme for coherence-enhancing diffusion filtering with optimized rotation invariance", Journal of Visual Communication and Image Representation, vol. 13(1-2):103-118 (2002).
Wong et al., "Quantification of fractional flow reserve based on angiographic image data", The International Journal of Cardiac Imaging, vol. 28(1):13-22 (2012).
Wong et al., "Determination of fractional flow reserve (FFR) based on scaling laws: a simulation study", Physics in Medicine and Biology, vol. 53:3995-4011 (2008).
Wong et al., "Automated technique for angiographic determination of coronary blood flow and lumen volume", Acad. Radiol. vol. 13:186-194 (2006).
Xu et al., "Snakes, shapes, and gradient vector flow", IEEE Transactions on Image Processing, vol. 7:359-369 (1998).
Yang et al., "Novel approach for 3-D reconstruction of coronary arteries from two uncalibrated angiographic images", IEEE Transactions on Image Processing, vol. 18(7):1563-1572 (2009).
Youssef et al., "Role of computed tomography coronary angiography in the detection of vulnerable plaque, where does it stand among others?", Angiology, vol. 1(2):1000111-1-1000111-8 (2013).
Zhang et al., "Quantification of coronary microvascular resistance using angiographic images for volumetric blood flow measurement: in vivo validation", Am J Physio Heart Circ vol. 300(6):H2096-H2104 (2011).
International Search Report and Written Opinion in application No. PCT/IB20/52879, mailed on Sep. 3, 2020, in 9 pages.

(56) References Cited

OTHER PUBLICATIONS

International Preliminary Report on Patentability and Written Opinion in application No. PCT/IB20/52879, dated Jul. 3, 2020, in 6 pages.
Office Action in Japanese application No. 2021-558763, dated Jan. 16, 2024, in 10 pages.

* cited by examiner

FIG. 5D
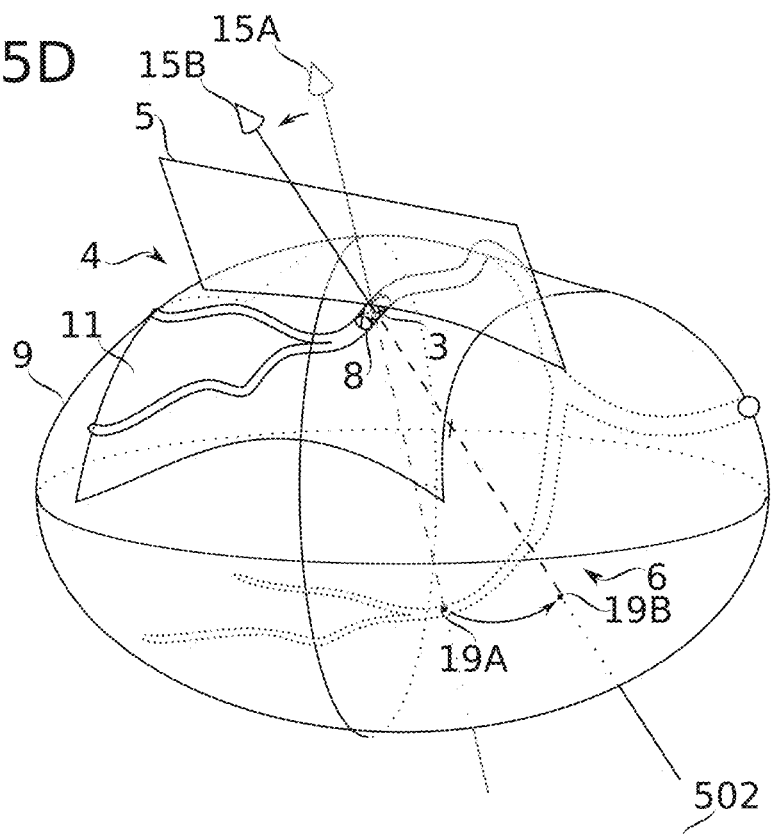
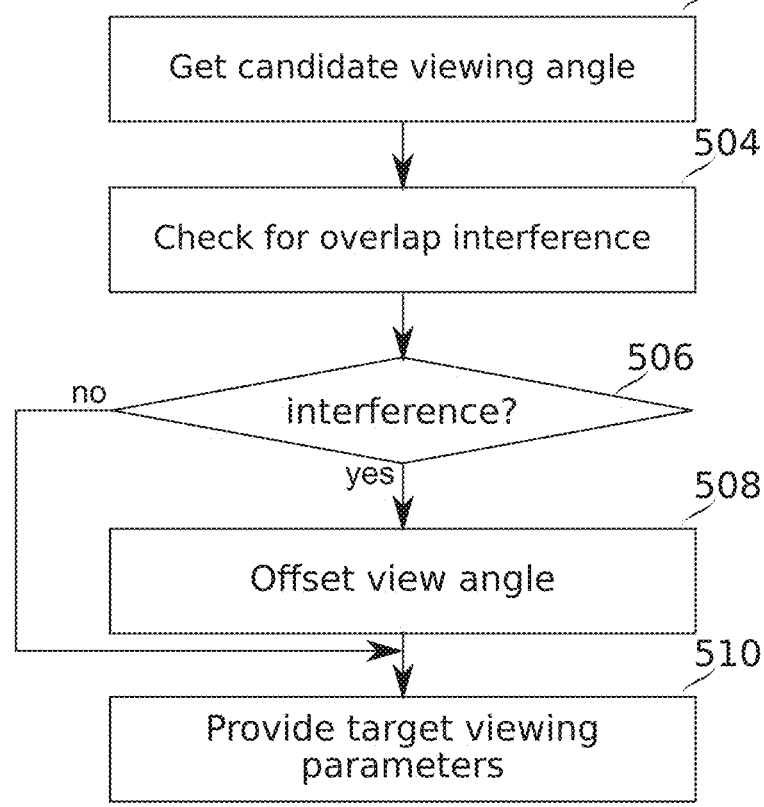
FIG. 5E

METHODS AND APPARATUS FOR ANGIOGRAPHIC IMAGE SELECTION

PRIORITY CLAIM

The present application is a national phase filing of International Application No. PCT/IB2020/052879, filed on Mar. 26, 2020, which claims priority to U.S. Provisional Patent Application No. 62/827,261, filed Apr. 1, 2019, the entire contents of each of which are incorporated herein by reference and relied upon.

TECHNICAL FIELD

The present invention, in some embodiments thereof, relates to the field of medical imaging and more particularly, to methods of determining medical imaging parameters for angiographic image selection.

BACKGROUND

Arterial stenosis is one of the most serious forms of arterial disease. In clinical practice, stenosis severity is estimated by using either simple geometrical parameters, such as determining the percent diameter of a stenosis, or by measuring hemodynamically based parameters, such as the pressure-based myocardial Fractional Flow Reserve (FFR). FFR is a measurement of the functional significance of coronary stenoses. An FFR measurement represents a ratio between a maximal blood flow in an area of stenosis and a maximal blood flow in the same area with the stenosis virtually removed. Earlier studies show that FFR<0.75 is an accurate predictor of ischemia and deferral of percutaneous coronary intervention for lesions with FFR≥0.75 appears to be safe.

In some instances, FFR is modeled using a plurality of two-dimensional (2-D) angiographic images that are recorded at different angles with respect to coronary arteries or vasculature of a subject. The angiographic images are analyzed to determine 2-D dimensions, curvatures, and other features along vascular extents, which are used to create a three-dimensional (3-D) coordinate system (or/or model). Oftentimes, a clinician may desire to view one or more angiographic images that correspond to a certain location on the 3-D model. Currently, a clinician has to manually review the angiographic images to find the desired view. As one can appreciate, this manual review can be time consuming and inefficient, especially if the patient is still undergoing treatment.

After FFR analysis, a clinician may perform a treatment by placing a stent into a portion of the patient's vasculature at a location of a stenosis or lesion. To confirm the placement is correct, one or more additional angiographic images are recorded and reviewed by the clinician. Typically, a clinician has to manually determine one or more angles with respect to the vasculature to acquire images that clearly show the stent, with minimal foreshortening, vessel overlap, or obstruction. In some instances, a clinician may have to record a second set of angiographic images if the first set does not adequately show the stent. Such a manual procedure is inefficient, time consuming, and potentially problematic for a patient undergoing treatment.

SUMMARY

The example system, method, and apparatus disclosed herein relate to an automatic calculation and/or selection of a viewing angle for an angiographic image. A viewing angle can impact on how clearly a certain target region of interest, such as a portion of a patient's coronary arteries, appears in an image. For example, foreshortening and/or overlap with other imaged features can interfere with measurement and/or verification (e.g., to check if a stent is fully deployed).

An aspect of some embodiments of the disclosure relates to selection of an available (pre-existing) image from among a plurality of available images, based on the evaluation of its viewing angle according to criteria. For example, selection of an image is made to minimize foreshortening and/or overlap in the image as a whole. Additionally or alternatively, an image may be selected for viewing one or more particular targets. In the field of vascular measurements, "foreshortening" generally refers to the apparent shortening of a longitudinal measurement of a blood vessel in an image due to the blood vessel being rotated so that the longitudinal extent of the blood vessel lies along a direction which is non-perpendicular to a viewing angle from which the blood vessel is imaged.

It is noted that the substantially radial symmetry of blood vessels means that depth foreshortening in the general sense that occurs with the imaging of any 3-D object is typically of little concern for the radial cross-section of blood vessels. A blood vessel with a round cross-section appears to have substantially the same radius from any direction, since a viewing angle that distorts one dimension of the cross-section will generally place another into perpendicular alignment with the viewing angle.

Features besides blood vessels may have a longitudinal or other axis of interest for measurement; and the term "foreshortening" is optionally applied to shortening in the apparent length of such an axis. Aggregate measures of foreshortening (e.g., for a set of blood vessel portions extending longitudinally in many different directions) may be created by averaging or otherwise weighting together metrics of foreshortening generated for blood vessel segments individually, or otherwise calculated.

An aspect of some embodiments of the disclosure relates to the use of a shell surface in choosing a viewing angle of minimal foreshortening of a target.

There is provided, in accordance with some embodiments of the present disclosure, a method of selecting an existing angiographic image. The method includes receiving a plurality of angiographic images, receiving a vascular model of a vasculature, and receiving a selection of a target region of the vascular model. The method also includes determining a viewing angle cost function that defines cost function values for a plurality of viewing angles with respect to the target region. The cost function values include a first set of cost function values that are located on a first, lower-cost side of the cost function threshold and a second set of cost function values that are located on a second, higher-cost side of the cost function threshold. The method further includes selecting an angiographic image from among the plurality of angiographic images, using the viewing angle cost function applied to the vascular model, by identifying an angiographic image that corresponds to a viewing angle having a cost function value that is located on the first, lower-cost side of the cost function threshold. Moreover, the method includes displaying the selected image.

In some embodiments, a set of viewing angles have cost function values that are less distant from the cost function threshold than the cost function value of the viewing angle of the selected image, and on the second, higher-cost side of the cost function threshold, is at least as large as a set of viewing angles on the first, lower-cost side of the cost function threshold.

In some embodiments, a set of angles have cost function values that are less distant from the cost function threshold than the cost function value of the viewing angle of the selected image, and on the second, higher-cost side of the cost function threshold, is twice as large as a set of angles on the first, lower-cost side of the cost function threshold.

In some embodiments, the viewing angle of the selected image is at a respective local minimum of the viewing angle cost function on the first, lower cost side of the cost function threshold.

In some embodiments, the viewing angle cost function value of the viewing angle of the selected image is within a same value distance from a respective local minimum of the viewing angle cost function, while remaining on the first, lower-cost side of the cost function threshold.

In some embodiments, the viewing angle of the selected image is within a same angular distance from a respective viewing angle having a local minimum of the viewing angle cost function, while remaining on the first, lower-cost side of the cost function threshold.

In some embodiments, the method further includes selecting a viewing angle corresponding to a viewing angle of the selected image, and obtaining a new image using the selected viewing angle.

In some embodiments, the method further includes selecting an imaging viewing angle near the viewing angle of the selected image, but with an offset from the viewing angle of the selected image. In these embodiments, the imaging viewing angle is selected according to a modified cost function that modifies the viewing angle cost function with a cost that increases according to a magnitude of the offset.

In some embodiments, the selecting is also based on a characteristic of a feature shown in the image.

In some embodiments, the feature is a degree of contrast filling of the vasculature modeled by the vascular model.

In some embodiments, the selecting is also based on the availability of further angiographic images that are recorded at a same heartbeat phase as the selected image.

In some embodiments, the selecting is also based on the availability of further images recorded within a certain time period of the selected image.

In some embodiments, the selected image and the further images together comprise a cineangiogram.

In some embodiments, the viewing angle cost function penalizes foreshortening due to offsets along a first angular axis defining rotations within a first plane less severely than it penalizes foreshortening due to offsets along a second angular axis defining rotations within a second plane, perpendicular to the first plane.

In some embodiments, the target region comprises a vascular segment defining a longitudinal axis, and the first plane is perpendicular to the vascular segment.

In some embodiments, a region of the cost function along the first angular axis has values within the range of values of a region of the cost function along the second angular axis.

In some embodiments, the viewing angle cost function is determined based on a direction perpendicular to the target region minimizing foreshortening of the target region, and angles offset from the perpendicular direction increasing foreshortening.

In some embodiments, the viewing angle cost function is calculated with increased cost for increasing view overlap of the target region with other regions of the vascular model.

In some embodiments, the viewing angle cost function is calculated with decreased cost for viewing angles that show areas of the vascular model with decreased vascular function more clearly.

In some embodiments, decreased vascular function is determined based on a calculated FFR value for regions of the vascular model.

In some embodiments, showing the areas more clearly comprises one or more of reducing their overlap with structures of the vascular model, and reducing their foreshortening.

In some embodiments, the target region comprises a vascular lesion.

In some embodiments, the vascular lesion is distributed among a plurality of vascular segments separated by a vascular branching point.

In some embodiments, the target region comprises a plurality of vascular branches identified by the position of the vascular lesion.

In some embodiments, the vascular model models an arterial vasculature, and the vascular branches are downstream branches of the vascular lesion.

In some embodiments, the target region comprises a primary target and a secondary target.

In some embodiments, the target region comprises a vascular stent.

In some embodiments, the determining the viewing angle cost function comprises calculating a shell representing a surface across which the vasculature extends.

In some embodiments, the shell comprises a substantially ovate surface.

In some embodiments, the ovate surface is defined between portions of the vascular model separated by at least 135° from one another relative to a geometric center of the ovate surface.

In some embodiments, the vasculature modeled by the vascular model comprises a portion of a cardiac arterial vasculature.

There is provided, in accordance with some embodiments of the present disclosure, a processor and memory configured to carry out the method described above.

There is provided, in accordance with some embodiments of the present disclosure, a method of choosing a viewing angle for an image, including receiving a vascular model of a vasculature, receiving a selection of a target region of the vascular model, and determining a viewing angle for viewing the target region. The method further includes providing the viewing angle for use in imaging the target region. In the disclosed method, determining the viewing angle includes calculating a shell representing a surface across which the vasculature extends, and determining a direction perpendicular to the shell on a portion of the surface across which the target region extends.

In some embodiments, the shell comprises a substantially ovate surface.

In some embodiments, the ovate surface is defined between portions of the vascular model separated by at least 135° from one another relative to a geometric center of the ovate surface.

There is provided, in accordance with some embodiments of the present disclosure, a method of choosing a viewing angle for an image, including receiving a vascular model of a vasculature, selecting a target region of the vascular model, and determining a viewing angle for viewing the target region. The method also includes providing the viewing angle for use in imaging the target region. In the disclosed method, determining the viewing angle includes evaluating a cost function that weights foreshortening of the target region differently on two perpendicular angular axes. The provided viewing angle foreshortens the target region on at least one of the two perpendicular axes.

In some embodiments, the foreshortening comprises viewing angle-dependent shortening of an imaged length of the target region, wherein the imaged length extends along a longitudinal axis of the target region, and wherein the imaged length is shortened relative to an actual length of the target region along the longitudinal axis.

There is provided, in accordance with some embodiments of the present disclosure, a method of choosing a viewing angle for an image, including receiving a vascular model of a vasculature, receiving a selection of a target region of the vascular model, and determining a viewing angle for viewing the target region. The method also includes providing the viewing angle for use in imaging the target region. In the disclosed method, determining the viewing angle includes determining a direction perpendicular to the target on a portion of the surface across which the target region extends, finding a plane containing an angular axis, containing the perpendicular direction, and around which foreshortening of a longitudinal axis of the target region is minimized when viewed from within the plane. The provided viewing angle is offset from the perpendicular direction within the plane, to a viewing angle from which overlap of the target region with other regions of the vascular model is removed.

In some embodiments, the provided viewing angle is offset to a minimum distance from the perpendicular direction to achieve a viewing angle from which overlap of the target region with other regions of the vascular model is removed.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 5B-5D schematically illustrate a method of mitigating an overlap condition for an image viewpoint, according to some embodiments of the present disclosure;

FIG. 5E is a schematic flowchart of the method of FIGS. 5B-5D, according to some embodiments of the present disclosure;

DESCRIPTION OF SPECIFIC EMBODIMENTS OF THE INVENTION

Figure 1A:
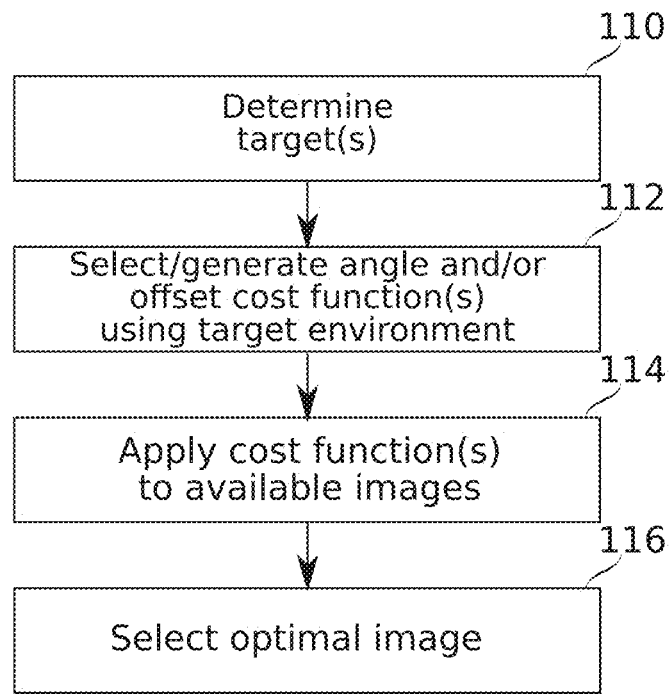
FIG. 1A is a schematic flowchart of a method of selecting an image, from among a plurality of images, obtained from an optimal available viewing angle of a target, according to some embodiments of the present disclosure.

The present invention, in some embodiments thereof, relates to the field of medical imaging and more particularly, to methods of determining medical imaging parameters.

Unless otherwise defined, technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, a method, an apparatus, and/or a computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, software or firmware, and/or a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in a method and/or by a system are performed by a data processor (also referred to herein as a "digital processor"), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device, such as a keyboard or mouse, are optionally provided. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

As provided herein, a data processor is said to be "configured" to perform certain data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing, and/or presenting processing results. Presenting optionally comprises showing on a display, indicating by sound, printing on a printout, or otherwise providing results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems), and/or computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Overview

An aspect of some embodiments of the disclosure relates to the automatic calculation and/or selection of a viewing angle for an angiographic image.

A viewing angle can affect how clearly a certain target region of interest appears in an image. For example, foreshortening and/or overlap with other imaged features can interfere with measurement and/or verification (e.g., to check if a stent is fully deployed). Target regions can also be associated with regions of primary interest (e.g., the location of a lesion, suspected lesion, and/or implanted stent), and regions of secondary interest (e.g., branches of the arterial vasculature downstream of the lesion, suspected lesion, and/or implanted stent). There may be a plurality of target regions, for example, lesions in two separate vascular branches.

Furthermore, costs, risks, and use of resources are potentially affected by the choice of a viewing angle for an angiographic image. For example one or more of the following may apply:

Radiation exposure to a patient should be minimized, which counter-indicates a trial-and-error approach to discovering a good viewing angle for imaging.

Procedure time for procedures to which angiography may be adjunct is preferably minimized, again discouraging use of trial-and-error.

Activities related to angiography such contrast injection may be practically limited in how many times they can be repeated during a procedure; imaging from an optimal angle initially may save repetitions.

Procedures involving angiography may be complex, so that manual choice of a viewing angle (even avoiding multiple attempts) represents an additional load on attention and/or staffing requirements.

Of a plurality of images already taken during a procedure, there may be some that show features of interest from an optimal or near-optimal viewing angle; but devoting attention during a procedure to the identification and selection of the image is potentially consuming of human time and resources.

For a new image, there may be a reason to match its viewing angle to an existing image, for example to assist in locating/orienting features in the new image with respect to features in the older image. Identifying and selecting which of a potential plurality of older images is well- and/or best-suited for serving as a viewing angle template is potentially consuming of human time and resources.

In some embodiments, an optimal imaging angle and/or a range of acceptable imaging angles for viewing one or more targets within a single image is calculated. The targets optionally comprise blood vessels, which may be distinguished, for example, by a disease state (e.g., stenotic lesion, chronic total occlusion) and/or the presence of a treatment implant such as a stent. Criteria optimization may be used for automatic image selection and, in some embodiments, include minimizing foreshortening and/or overlap in the view with other features.

In some embodiments, a cost function (or, potentially equivalently, a value function which varies inversely with the cost function) is used to determine the optimal image angle and/or range of angles.

Optionally, a viewing angle for selecting an existing image is presented to a user explicitly in terms of direct device settings (e.g., position angles). Optionally or additionally, an existing image is itself presented. Optionally or additionally, a plurality of images are presented for selection by a user (for example, from a list of names/properties, and/or from presentations of the images themselves), together with an indication of their preferability (e.g., equivalently preferable, or one or more preferable in one or more respects).

Optionally, settings for a new image are presented to a user explicitly in terms of direct device settings (e.g., position angles). Optionally or additionally, settings for the new image are presented to the user as choices related to the existing image (e.g., "image from the angle of this image", where this image may be displayed and/or indicated by name and/or properties). Optionally, settings for a new image are chosen and used to control an imaging device directly and automatically, optionally with an opportunity for a user to override and/or indicate acceptance.

An aspect of some embodiments of the disclosure relates to selection of an available (pre-existing) image from among a plurality of available images, based on the evaluation of its viewing angle according to criteria, for example, of minimizing foreshortening and/or overlap in the image as a whole, and/or of one or more particular targets in the image.

In some embodiments, the viewing angle of the selected image is not an optimal image with respect to minimizing either foreshortening avoidance, or overlap reduction, or both jointly, due to limitations in which images are available. For example, the selected image's viewing angle may be at least 5°, 10°, 15°, or another angle away from a viewing angle that is determined to be optimal, apart from limitations imposed by available choices.

Additionally or alternatively, in some embodiments, a set of preferred viewing angles have cost function values on one side of a threshold. For example, if the cost function evaluates to a scalar, the threshold is a scalar, and cost function values, e.g., below the threshold are preferred viewing angles. There may be a single preferred viewing angle, in which case the threshold is optionally defined as a value nearest to the preferred viewing angle. There may be a discrete number of preferred viewing angles on the same side of the threshold, e.g., local cost function minima. Optionally, preferred viewing angles are within a same cost function value distance to their nearest local minimum (i.e. consistent with also remaining on the same side of the threshold). Additionally or alternatively, preferred viewing angles are within a maximum angle difference from the viewing angle of their nearest local minimum.

In some embodiments, the viewing angle of a selected angle, selected using the cost function, is on an opposite side of the threshold from the set of preferred viewing angles. In some embodiments, there are at least as many viewing angles "as bad or better" than the viewing angle of the selected image (e.g., at or closer to the cost function threshold) as preferred viewing angles.

In some embodiments, images evaluated for viewing angle are jointly evaluated for another criterion, for example, contrast agent filling, presence in a time series, matching of a certain heartbeat phase, or another non-angle criterion.

In some embodiments, an existing image chosen for having an optimal viewing angle (optionally optimal jointly with other criteria) is used for selecting a viewing angle for a new image to be taken. In some embodiments, the viewing angle of the existing image is used for the new image. In some embodiments, the viewing angle of the new image is selected jointly for criteria of matching the existing image within some tolerance (e.g., as evaluated by a cost function), and for showing a certain target such as a stent and/or blood vessel lesion with minimal foreshortening and/or overlap with other features in the image.

An aspect of some embodiments of the disclosure relates to the use of a shell surface in selecting a viewing angle of minimal foreshortening of a target. In some embodiments, a target for viewing includes a blood vessel, which is part of a vascular network extending around a portion of an organ's surface (e.g., surface of a heart). In some embodiments, a model (shell) approximating a shape of the organ surface is calculated using the global structure of a blood vessel model, where the model includes vessels anatomically known to extend across the organ's surface.

In some embodiments, the shell is used to determine the orientation of a plane that is tangent to the organ at a given location. In particular, the given location in some embodiments is a viewing target, and a ray perpendicular to the shell tangent plane optionally represents a preferred viewing angle (and/or its reflection) with respect to the criterion of foreshortening: it represents the viewing angle from which vascular structures at the position of the viewing target are least foreshortened.

Herein, angles from a reference point and falling within a single plane containing that reference point are also referred to as comprising a first "angular axis" (optionally referred to as the azimuth axis). Viewing angles pointing toward a reference point and rays pointing away from the reference point may be considered inverse equivalents of each other).

To obtain other angles in a three-dimensional space, a second angular axis (optionally referred to as the elevation axis) may be defined as the angular offset from the plane of the first angular axis, for a ray extending from the reference point to a position outside the plane of the first angular axis (or if the ray remains within that plane, the offset is 0°). Angles of a line or ray not passing through the reference point can be expressed using the first and second angular axes, by assigning angular values according to a ray that is parallel to the line or a ray that does include the reference point. Herein, the first and second angular axes (azimuth and elevation axes) are also referred to as perpendicular angular axes.

In some embodiments, an image target comprises a substantially cylindrical shape defining: a longitudinal axis, and a plane lying perpendicular to the longitudinal axis. The perpendicular plane, in some embodiments, is understood to define the first angular axis (azimuth axis). Optionally, a cost function for evaluating foreshortening effects of a viewing angle onto the image target penalizes offsets to sub-optimal image angles in the azimuth axis less then sub-optimal image angles of similar magnitude along an angular axis within a plane containing the longitudinal axis (elevation axis). In some embodiments, angular offsets along either or both angular axes are weighted so that they lead to potential viewing angle selections in combination with other criteria, such as feature overlap.

In some embodiments, the other criteria comprise image criteria related to features other than viewing angle, for example, degree of contrast filling and/or heartbeat phase, and the criteria are weighted together to generate a joint compromise, for example, a compromise between optimal image contrast and/or heartbeat phase, and optimal viewing angle.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Methods of Selecting and/or Generating Viewing Angles

Reference is now made to FIG. 1A, which is a schematic flowchart of a method of selecting an image, from among a plurality of images, obtained from an optimal available viewing angle of a target, according to some embodiments of the present disclosure.

At block 110, in some embodiments, a target to be imaged is determined. The target, in some embodiments, comprises a single contiguous region. Optionally the single contiguous region is defined by the extents of a blood vessel segment and/or device implanted in or near a blood vessel segment. In some embodiments, the blood vessel is modeled substantially as a cylinder having a longitudinal axis. Optionally, the single contiguous region is defined as an area or volume extending from a center or other reference. Optionally, the single contiguous region comprises blood vessels within a certain area or volume extending from a center or other reference.

In some embodiments, the target comprises a plurality of separately, defined regions, optionally contiguous, non-contiguous, and/or overlapping.

Typical target regions include lesioned blood vessels (e.g., stenotic lesions) and/or stented blood vessels. Target regions may also include bifurcations, trifurcations, and/or curvatures in blood vessels, such as coronary arteries.

At block 112, in some embodiments, one or more cost functions for an image viewing angle (optionally including costs for different centers of the image view) are determined. The image viewing angle cost function is optionally constructed according to any of the methods described herein. For example, the image viewing angle cost function is calculated using elements of the embodiments described in relation to FIGS. 1C-13D. In some embodiments, the image viewing angle cost function is configured to minimize one or both jointly of foreshortening of the target and overlap of the target with other features in the image. In some embodiments, additional cost criteria are evaluated and applied, for example as described in relation to the figures herein.

At block 114, in some embodiments, the cost function(s) of block 112 are evaluated with respect to the viewing angles of a plurality of available images.

At block 116, in some embodiments, the image(s) which are optimal with respect to the evaluated cost function(s) are selected. Optionally, a selected image is presented for display. Optionally, the viewing angle of a selected image is used for further operations. For example, the viewing angle of a selected image is used to set the viewing angle of a new image, and/or used as a part of the criteria for selection of a new image's viewing angle, e.g., in conjunction with use of the method of FIG. 1B.

Figure 1B:
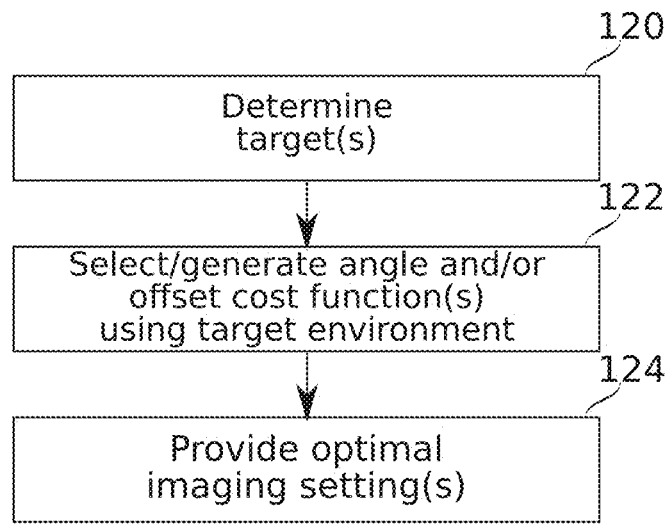
FIG. 1B is a schematic flowchart of a method of selecting an optimal available viewing angle of a target for use in imaging, according to some embodiments of the present disclosure.

Reference is now made to FIG. 1B, which is a schematic flowchart of a method of selecting an optimal available viewing angle of a target for use in imaging, according to some embodiments of the present disclosure.

At block 120, in some embodiments, targets are determined, for example as described in relation to block 110 of FIG. 1A.

At block 122, in some embodiments, an image viewing angle cost function (optionally including costs for different centers of the image view) is determined, for example, as explained in relation to block 112 of FIG. 1A (e.g., minimizing foreshortening and/or overlap with other image features). Optionally, a viewing angle's optimality relies jointly on further criteria such as similarity of the viewing angle to an existing image's viewing angle, context of the image within a procedure (e.g., obtained at a particular heartbeat phase, obtained as part of a cineangiogram comprising a plurality of similar images, and/or obtained during a period of good contrast filling of blood vessels). A cineangiogram, as the term is used herein, refers to a set of angiographic images which are sufficiently similar that they can, for example, be displayed in sequence as a short "movie clip". A cineangiogram provides information about one or more dynamic features of the imaged target, and/or features of the imaged target that are revealed by changes in imaging settings such as viewing angle, irradiation wavelength, filtering, or another parameter. A typical image frame acquisition rate for a cineangiogram is about 15-30 Hz, but other frequencies may be used. Optionally, a cineangiogram is compiled from images taken at wider intervals. For example, images obtained at times synchronized to a certain phase of a heartbeat cycle may be combined from several heartbeat cycles. Some cineangiograms comprise (and/or can be readily modified to create) images similar enough to one another that they can be analyzed by image comparison techniques such as digital subtraction.

At block 124, in some embodiments, the cost function is evaluated, and the optimal image settings provided.

Figure 1C:
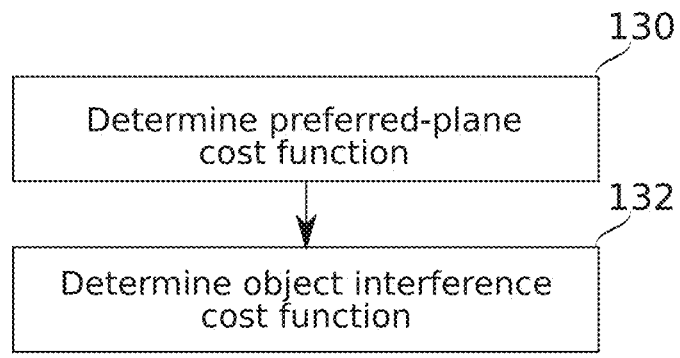
FIG. 1C is a schematic flowchart of a method of considering cost functions in selecting an optimal available image angle and/or angle for use in imaging, according to some embodiments of the present disclosure.

Reference is now made to FIG. 1C, which is a schematic flowchart of a method of considering cost functions in selecting an optimal available image angle and/or angle for use in imaging, according to some embodiments of the present disclosure. This is an example, for some embodiments, regarding the construction of a cost function, e.g., at block 112 or 122 of FIGS. 1A-1B.

At block 130, in some embodiments, a preferred-plane cost function is chosen. This comprises a cost function that selects a plane which runs generally parallel to a plane defined by a region targeted for imaging (for example, as described in relation to FIGS. 4A-4B). The cost function can comprise, for example, a distance minimizing method of matching a plane to a set of features at, surrounding, and/or connected to a particular target of interest. In some embodiments, the cost function comprises estimating a surface (e.g., of a shell or portion thereof) which blood vessel targets occupy, with the preferred plane being the plane which is tangent to the surface in the region targeted for imaging (e.g., at the region's center and/or at a selected point). In some embodiments, a plurality of planes is "optimal", in the sense that they each are associated with an equivalent balance of criterion costs.

In some embodiments, the preferred plane is associated with a viewing angle (and optionally its reflection) oriented perpendicular to the preferred plane. In some embodiments, the notion of a preferred-plane (or range of such planes) is equivalently augmented or replaced with a preferred viewing angle (or range of such angles) perpendicular to the preferred plane. For purposes of explanation, figures herein show rays drawn from targets to potential viewing points. It should be understood that viewing angles are back along these rays (e.g., from a position on the ray) to the target. For each ray there is also a reflected version of the ray which is potentially equivalent in defining a viewing angle, except that the view is mirror-imaged from the side of the reflected ray. For the purposes of the examples given, except as otherwise noted to point out specifics, the viewing angle is from the center of a sensing plane of the imaging device (e.g., the center of the imaging sensor) and chosen so that the target is centered in the image. Nevertheless, this does not preclude determining imaging directions for images which include slew parameters, e.g., which place a target "off center" in the image. This can be meaningful, for example, when a certain primary target is used to find an optimal, primary target-centered imaging angle, and then a slew is introduced (for example, to ensure that one or more secondary targets are within view) which places the primary target off-center, although still viewed from very nearly the same direction.

In some embodiments, even the concept of a "preferred" perpendicular viewing angle is unused, and a cost function is instead established for a range of viewing angles (optionally all viewing angles, optionally any subset of viewing angles) without singling out of and/or regard for a specific "perpendicular" angle. However, for purposes of explanation, embodiments herein are described as though an angle that is perpendicular to the local orientation of blood vessels and/or a shell along which the blood vessels lay sets a frame of reference around which angular cost functions can be constructed.

At block 132, in some embodiments, a second cost function part is determined. Penalties apply to angles from which the target (e.g., any primary or secondary target, or portion thereof) overlaps with other features of the image. Overlap may be determined in different ways, for example as described in relation to FIGS. 5A-5E.

Optionally, further cost functions are generated for use in the evaluation of other image and/or viewing angle-related criteria.

Viewing Angle Evaluation

Figure 2A:
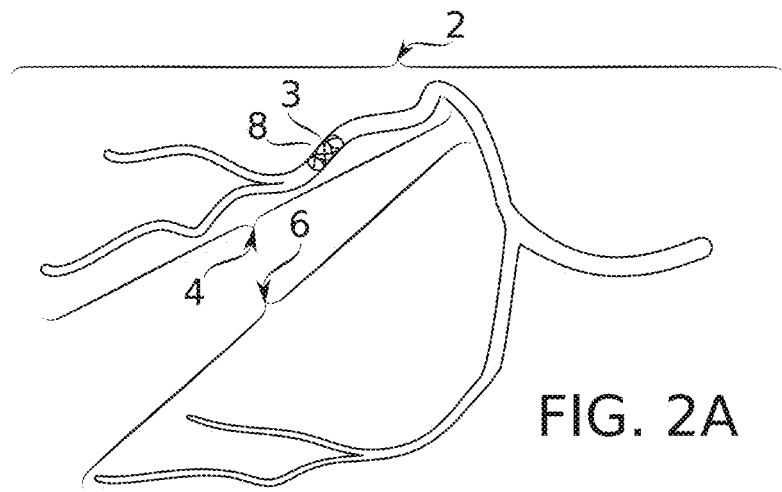
FIGS. 2A-2B schematically illustrate 3-D extents of a vasculature, according to some embodiments of the present disclosure.
Figure 2B:
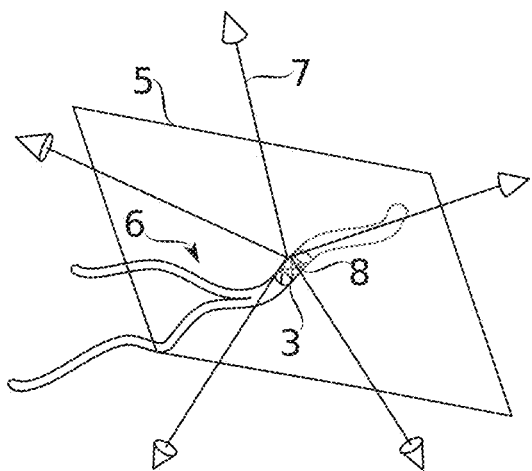

Reference is now made to FIGS. 2A-2B, which schematically illustrate 3-D extents of a vasculature 2, according to some embodiments of the present disclosure.

Vasculature 2, in some embodiments, comprises a portion of a coronary arterial vasculature. Vasculature 2 is not necessarily drawn in the figures to represent details of a particular anatomical vasculature such as a cardiac vasculature, but rather is provided as a simplified example.

In some embodiments, a target region 3 is a portion of the vasculature 2. Additionally or alternative, in some embodiments, the target region 3 comprises a structure 8 (for example, a vascular stent), which may be of particular interest for analysis using a 2-D image of the structure 8. The analysis quality may be partially dependent on how the structure 8 is shown in the 2-D image; e.g., how much of the structure 8 is foreshortened by the imaging angle, and how well-separated the structure 8 is from other structures in the image.

In some embodiments, the target region 3 is located within a vascular neighborhood 4, comprising blood vessels of the vasculature 2 that are nearby (e.g., adjacently connected to) the target region 3.

In some embodiments, one criterion for a preferred viewing angle (e.g., from a viewpoint located along ray 7) of the vascular target region 3 is how closely the viewing angle aligns with a plane 5 (FIG. 2B) passing orthogonally through an axis of the vascular target region 3 and passing longitudinally along the local orientation of the vascular lumen.

It is noted, however, that the vascular target region 3 is not necessarily composed of a single vascular segment having a well-defined longitudinal axis. For example, the target region 3 optionally comprises a diffuse lesion around a vascular branch, with different portions of the lesion (and/or of a stent inserted to that lesion portion) having different orientations. For example, the target region 3 may include a plurality of vascular segments separated by a vascular branching point. This can affect how foreshortening due to a viewing angle affects each particular lesion portion. Determination of viewing angles for compound feature targets is also discussed, for example, in relation to FIGS. 10A-11C.

In some embodiments, nearby vascular portion 6 comprises additional blood vessels of the vasculature 2. In some embodiments, the nearby vascular portion 6 comprises blood vessels, when viewed from some viewing angles, that potentially interfere with the imaging of the vascular target region 3. Herein, the vascular portion 6 is used as an example of a feature which potentially interferes with the imaging of the vascular target region 3 (e.g., the vascular portion 6 partially obscures the vascular target region 3 at certain imaging angles). However, it is to be understood that other features could also interfere with imaging, such as implants and/or osseous structures.

Figure 3:
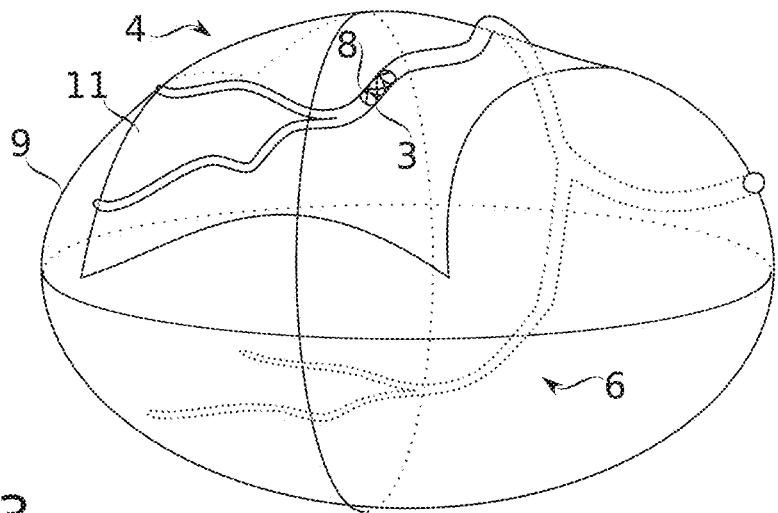
FIG. 3 schematically illustrates a 3-D shell extending along at least some of the extents of vasculature, according to some embodiments of the present disclosure.
Figure 4A:
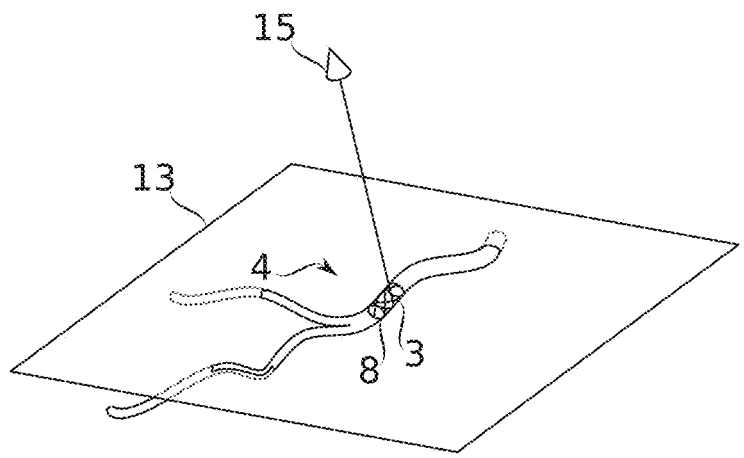
FIGS. 4A-4B schematically illustrate examples of planes extending approximately parallel to a plane that is tangential to a shell in the vicinity of a vascular target region, according to some embodiments of the present disclosure.
Figure 4B:
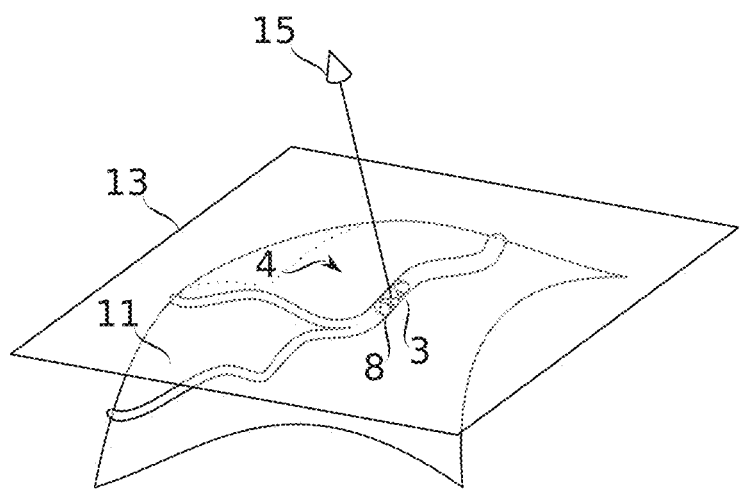

Reference is now made to FIG. 3, which schematically illustrates a 3-D shell 9 extending along at least some of the extents of the vasculature 2 shown in FIGS. 2A and 2B, according to some embodiments of the present disclosure. Reference is also made to FIGS. 4A-4B, which schematically illustrate examples of planes 13 extending approximately parallel to a plane that is tangential to the shell 9 in the vicinity of the vascular target region 3.

In certain imaging methods, for example X-ray imaging of the heart after contrast agent injection to its vasculature, blood vessels may be the primary high-contrast features visible in the image. In some imaged organs, for example the heart, the same blood vessels may be arranged generally along the extents of a 3-D surface approximating a substantially globular and/or ovate shell (e.g., shell 9), or portion thereof (e.g., surface 11). Optionally, the shell is defined for all angles around a geometrical center of the shell. Optionally, the shell extends between blood vessels (vascular segments) separated by at least 90°, at least 135°, at least 150°, or another angular distance relative to a geometrical center of an ovate shape that at least corresponds to the shell.

In some embodiments, a criterion for a preferred viewing angle (e.g., from a viewpoint located along ray 15) is how closely the viewing angle aligns with an angle that is perpendicular to a plane 13 tangent to surface 11 at about the position of target region 3, where the target region 3 comprises a position generally lying on surface 11. Ray 15 shows one perpendicular direction pointing generally outward from the shell 9. However, it should be understood that it may be equivalent for imaging purposes to image from near to the other perpendicular angle, 180° rotated from the ray 15.

Viewing angles that are close to the perpendicular angle are potentially more likely to show both the target structure 8 in the target region 3 and its immediate neighborhood (e.g., the vascular neighborhood 4) with minimal foreshortening.

Plane 13 can be estimated in different ways. However, the results of different methods may not always be equivalent.

In some embodiments (FIG. 4A), plane 13 is estimated from the locations of portions of vascular neighborhood 4 surrounding target region 3. In some embodiments, for example, the vascular neighborhood 4 is defined as comprising the vascular positions within a certain distance of a center of the target region 3. The distance may be Euclidean, for example (i.e., within a circle or sphere of some radius). Optionally, another distance metric is used, for example, distance traveled along connected blood vessel portions. An orientation of the plane 13 can then be estimated, for example, as the plane having the best least mean squares fit to the positions of blood vessel portions within the vascular neighborhood 4.

Optionally, the best-fit plane is determined, for example, by finding the plane P (corresponding to plane 13) that minimizes the cost function shown below in Equation (1):

$$\Sigma_j K_j d(j,P) \qquad (1)$$

Where $d(j,P)$ is a distance function calculated between some candidate plane P and each of a plurality of the portions of vascular neighborhood 4 (iterated over by j). The factor $K_j$ is an optional weighting coefficient allowing some portions to contribute more than others to the fitted plane. Optionally portion contributions to the sum are weighted (e.g., by adjusting the value of $K_j$) by their size, position relative to the target region 3, and/or another parameter of significance. For example, a sub-region comprising a stent and/or a blood vessel extent adjoining a stent may be assigned extra weight in the cost function.

For purposes of calculation, the portions of the vascular neighborhood 4 may be divided to any suitable size, optionally the same size (e.g., same lengths of a blood vessel if the target region is defined by blood vessel extents, or same area if defined by areas that are demarcated by the positions of blood vessels).

Potentially, however, the target region 3 is in a region which lacks enough branching structure of the vascular neighborhood 4 to obtain a well-defined tangent plane. For example, an unbranched blood vessel extending straight along a surface may provide insufficient information to constrain a plane to a single well-defined orientation. When the vasculature 2 does branch, it may be at a location which results in insufficient and/or misleading information as to the orientation nearer to the target region 3.

Alternatively, in some embodiments, the surface 11 of shell 9 relative to vasculature 2 is estimated by calculation (FIG. 4B). This may be, e.g., from knowledge of the 3-D extents of the vasculature 2; and/or by a method which jointly estimates the shell and the 3-D extents of the vasculature 2, for example as described in International Patent Publication No. 2018/165478 entitled "Shell-constrained localization of vasculature".

From the calculation of the surface 11, plane 13 is calculated in some embodiments, e.g., as a tangent plane. For example, plane 13 is a tangent plane that is calculated from the estimate of the orientation of the surface 11 at target region 3.

Figure 5A:
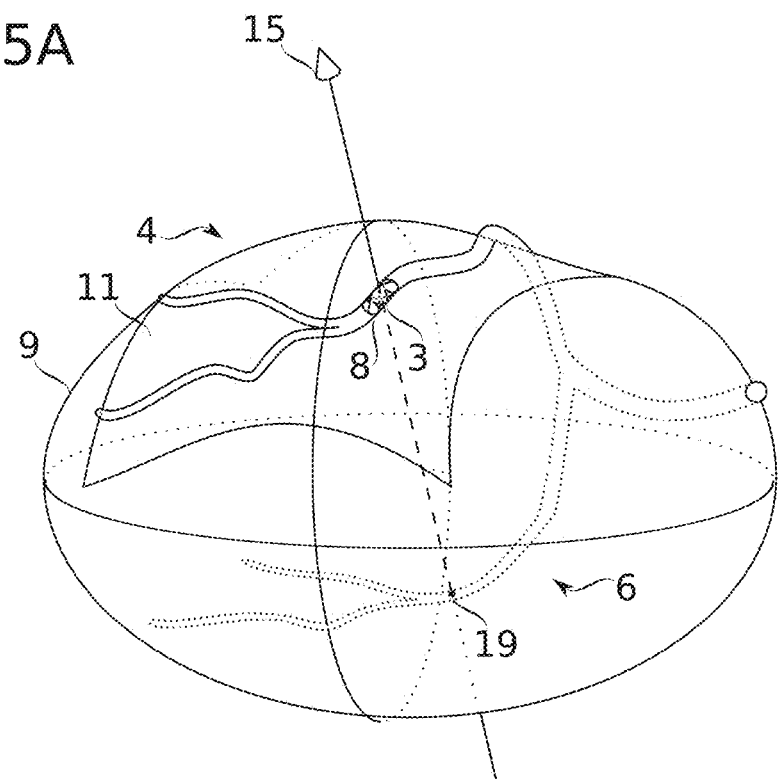
FIG. 5A schematically illustrates an overlap condition for an image viewpoint located along a ray, according to some embodiments of the present disclosure.

Reference is now made to FIG. 5A, which schematically illustrates an overlap condition for an image viewpoint that is located along a ray 15, according to some embodiments of the present disclosure.

The example ray 15 is oriented generally perpendicular to where it intersects surface 11. In the example shown, a region 19 of nearby vascular portion 6 happens to appear to underlie target region 3 as seen from positions along ray 15 since the region 19 is located on an opposite side of the shell 9 from the target region 3. From viewpoints outside of shell 9 but closer to the region 19 than the target region 3, the region 19 appears to overlie the target region 3, and the effect of obscuring visibility of the target region 3 would be similar. Herein, any condition where a target region 3 is partially obscured in an image due to proximity to another feature such as region 19 is referred to as "viewing overlap" (emphasizing that the overlap is from a particular viewing angle), or equivalently "overlap" or "overlapping".

In some embodiments, overlapping is mitigated and/or prevented by adjusting an imaging angle and/or a preferred imaging angle for a selected image.

Potential overlapping of a certain imaging angle (e.g., imaging of the target region 3 from a position along the ray 15) is detected, in some embodiments, by analyzing a simulated 2-D image of a 3-D model of the vasculature 2 that is recorded from that imaging angle; and/or analyzing the simulated imaging conditions. The simulated image and/or conditions is analyzed for proximity of the target region 3 with any region of the vasculature 2 to create an interfering region 19. Optionally, other structures (e.g., implants and/or osseous structures) are accounted for by adding them to the 3-D model; and/or by including them in a separately analyzed 3-D model, relative to which the position of the target region 3 can be estimated. Examples of simulated 2-D images of 3-D models of vasculature are shown, for example, in FIGS. 12A, 12C, and 12E, herein.

Figure 5B:
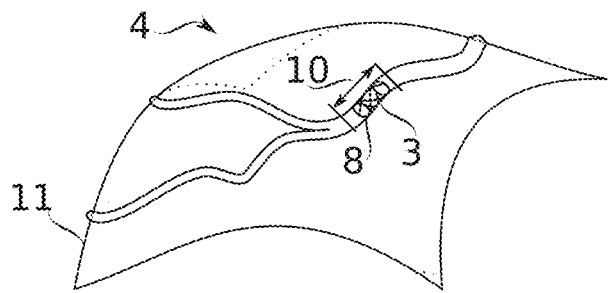
Figure 5C:
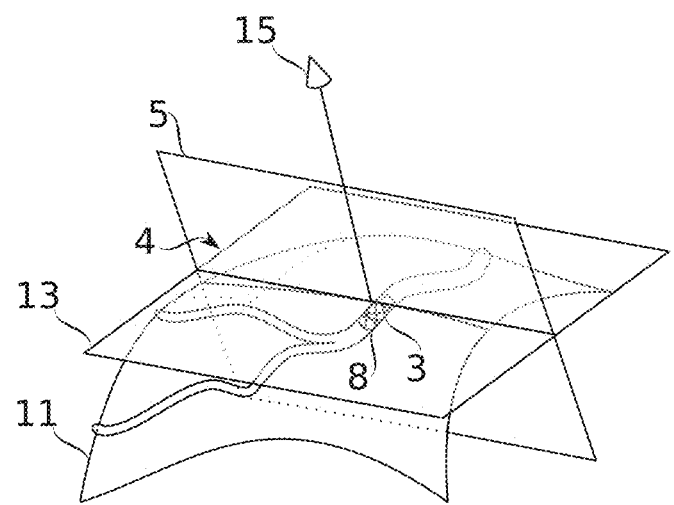

Reference is now made to FIGS. 5B-5D, which schematically illustrate a method of mitigating an overlap condition for an image viewpoint, according to some embodiments of the present disclosure. Reference is also made to FIG. 5E, which is schematic flowchart of it) the method of FIGS. 5B-5D, according to some embodiments of the present disclosure.

In some embodiments, a detected overlap is mitigated by adjusting an imaging angle so that instead of imaging from a position directly along ray 15, the position is offset within plane 5 enough to separate region 19 from the target region 3 in the image. Optionally, the plane 5 (FIG. 5C) is estimated as a plane perpendicular to an axis of the target region 3 that extends longitudinally along the lumen of a blood vessel segment 10 (FIG. 5B) passing through the target region 3.

This axis may be obtained, for example, from the 3-D reconstruction of the vasculature 2.

FIG. 5D shows an example illustrating the result. In this example, a new imaging angle 15B is selected (instead of angle 15A, which also corresponds to angle 15), which results in potentially overlapping region 19A being shifted away from the target region 3 in a potentially recorded image.

The result may be understood as implementing an algorithm like that of FIG. 5E, wherein at block 502, in some embodiments, a candidate viewing angle (e.g., from a position looking back along a ray 15A) is chosen. In some embodiments, the candidate viewing angle is a viewing angle normal to a surface 11 at a target region 3. Optionally, another method is used to select the candidate viewing angle, for example, as described in relation to ray 15 and FIG. 4A.

At block 504, in some embodiments, the candidate viewing angle is checked for overlap interfering with the viewing of the target region 3 and/or another structure. In some embodiments, the viewing interference is checked by using a simulated 2-D projection of a 3-D model of the vasculature 2 as seen from a position along the candidate viewing angle indicated by ray 15A. In some embodiments, overlap and/or near-overlap is calculated as described in relation to FIG. 5F. It should be noted that overlap need not be exact for it to be a potential source of interference; e.g., nearby parallel blood vessels potentially create mutual distraction during inspection and/or analysis, even if they do not actually obscure each other.

At block 506, in some embodiments, the flowchart branches depending on whether viewing interference is detected in block 504.

If there is viewing interference, then at block 508, the view is offset, for example, by adjusting the viewing angle. In some embodiments, the adjustment comprises offsetting the candidate viewing angle along a plane orthogonal to a longitudinal axis of a blood vessel that extends through the target region 3, for example, as described in relation to FIGS. 5B-5D. In some embodiments, adjustment of the viewing angle in practice comprises a translation. For example, the center of the optical (imaging) axis is translated, which potentially has the effect of changing the viewing angle with respect to the target region 3 without adjusting the angle of the imaging device itself.

The angular offset distance may be chosen in different ways. For example:
  As a single angular offset (e.g., of about 10°).
  Stepwise (e.g., in steps of about 1°), with evaluation after each step to check if the viewing interference is removed, and optionally that no new viewing interference is created).
  According to the results of a range-calculated cost function, for example as described in relation to FIGS. 6A-8.

Next, or if there is no interference, the candidate viewing angle is provided (at block 510) as the selected viewing angle. Blocks 502-508 are optionally an implementation of block 112 of FIG. 1A, and/or block 122 of FIG. 1B.

In some embodiments, the selected viewing angle is used to set a new imaging angle from which an image is to be taken, e.g., corresponding to block 124 of FIG. 1B.

In some embodiments, the selected viewing angle is used to select an image taken from among a plurality of images, with the viewing angle from which the selected image is taken being used in the selection criterion, e.g., corresponding to blocks 114-116 of FIG. 1A.

Figure 5F:
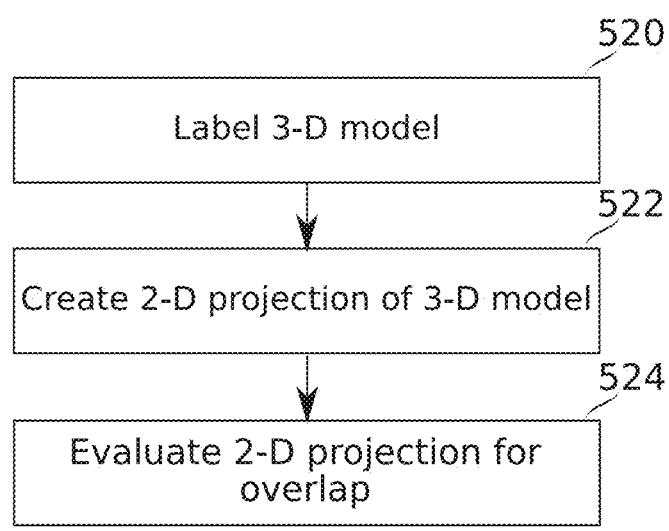
FIG. 5F is a flowchart schematically describing a method of detecting overlaps within a 2-D projection of a 3-D model, according to some embodiments of the present disclosure.

Reference is now made to FIG. 5F, which is a flowchart that schematically describes a method of detecting overlaps within a 2-D projection of a 3-D model, according to some embodiments of the present disclosure.

At block 520, in some embodiments, a 3-D model is optionally labeled by region. The labeling can be quantized (e.g., by tagging of different blood vessel segments), or simply comprise the existing three-dimensional coordinates of elements of the 3-D model.

At block 522, a 2-D projection image of the 3-D model is produced, using a certain angle to be analyzed for structure overlap. Optionally, as elements of the 3-D model are mapped to the 2-D projection image, their 2-D projections remain associated with the region information established in block 520.

At block 524, in some embodiments, the 2-D projection image is evaluated for overlap. In some embodiments, the evaluation is performed specifically in the region which corresponds to the 2-D projection of a target region 3. Optionally, more regions, e.g., the whole 2-D projection image, are checked.

Evaluation for overlap, in some embodiments, comprises checking to see if a same region of the 2-D image contains contributions from two or more different regions of the 3-D model. "Same region" is optionally a pixel, in which case only direct overlap will be detected. The range of direct overlap can be extended, e.g., by expanding the widths of the blood vessels in the 3-D model to be at least as large as the range at which overlap/near overlap is to be detected. One method of detecting overlap in such an embodiment (which does not necessarily require the explicit tracking of 3-D model regions as described in block 520) is to sum for each pixel the number of times that a ray extending through it from the viewing point also intersects the 3-D model. When the value is two or more, overlap is detected.

Additionally or alternatively, a "same region" can be expanded to any suitable size, e.g., by use of a neighborhood convolution of an image, Euclidean distance calculation, or another method. Regions can be overlapping within the image, e.g., defined to a certain distance with respect to each pixel position within the 2-D image.

In some embodiments, if a same region contains portions of two different blood vessel segments which are not directly connected to each other, then it is likely that they represent an overlap and/or near-approach condition which could potentially interfere with viewing of one or more of them. This condition is optionally counted as indicating an overlap.

In another example, in some embodiments, the region labeling instead uses the original 3-D model positions. In a coronary vasculature, for example, overlaps among vascular positions being viewed from a viewing angle nearly orthogonal to those vascular positions (e.g., perpendicular to shell 9) are potentially most likely to occur between relatively distant 3-D model positions (compared to the size of the "same region"). Thus, the occurrence within a certain 2-D region of 3-D model positions that are separated by significantly more than a diameter of the 2-D region (e.g., more than 20%) are likely to represent overlap or near-overlap, as two distinct portions of the vascular tree happen to cross through the same 2-D projection region.

Figure 9A:
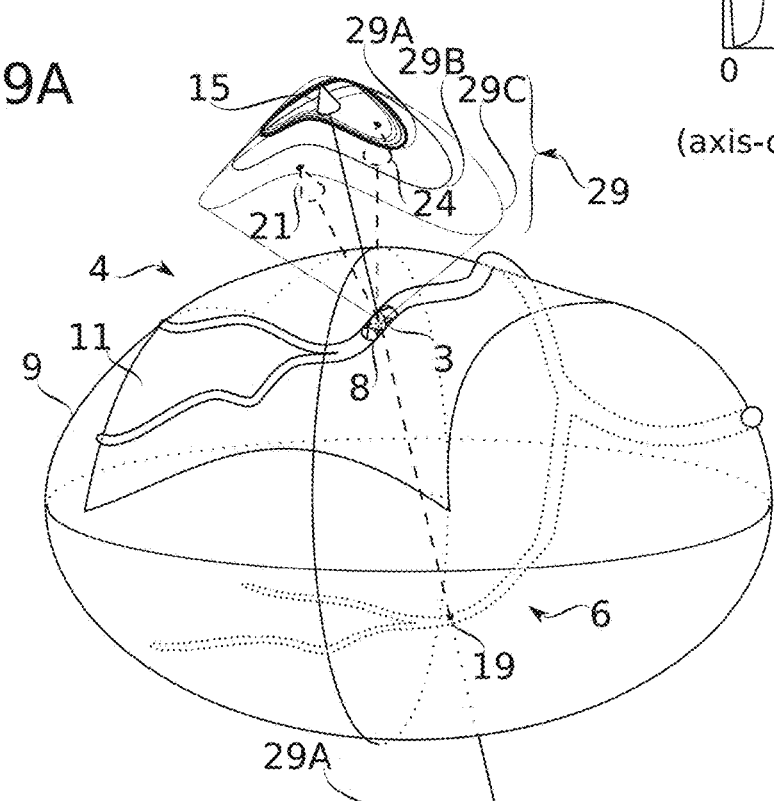
FIG. 9A schematically illustrates effects on a two-angular axis cost function due to overlap of a target region by an interfering region, and selection of an image according to its viewing angle and the overlap-adjusted cost function, according to some embodiments of the present disclosure.
Figure 9B:
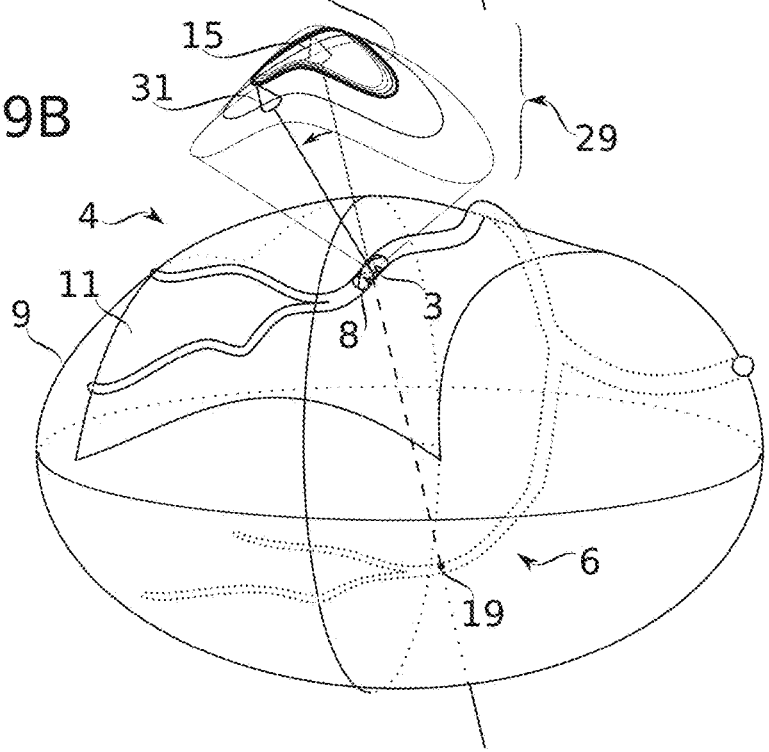
FIG. 9B schematically illustrates effects on a two-angular axis cost function due to overlap of a target region by an interfering region, and selection of an image according to its viewing angle and the overlap-adjusted cost function, according to some embodiments of the present disclosure.

After block 524, the overlap calculation is provided for use, e.g., at block 504 in the method of FIG. 5E, and/or in the generation of a cost function, for example as described in relation to FIGS. 9A-9B.

It is noted in particular that overlap detection need not be scored equally for all parts of the 3-D model and/or the 2-D projection. When a singular target region 3 is selected, it may be advantageous to set a large distance for overlap/near overlap detection, but only check the part of the 2-D projection corresponding to target region 3 itself for overlap. In some embodiments, overlap in any region is optionally considered as more-or less "costly", depending on where it occurs. Cost functions are described further in relation, for example, to FIGS. 7-11C.

Complex Criteria for Viewing Angle Evaluation

Figure 6A:
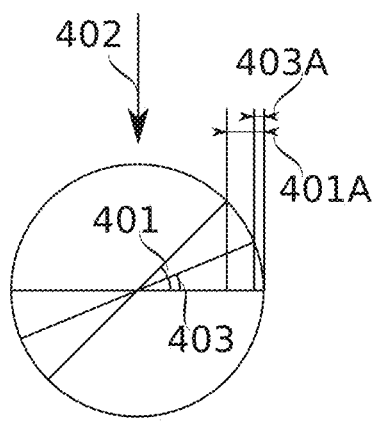
FIG. 6A schematically illustrates non-linear effects of angle changes on foreshortening effects, according to some embodiments of the present disclosure.
Figure 6B:
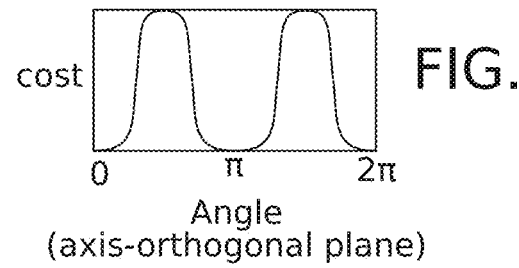
FIGS. 6B-6C schematically illustrate non-linear cost functions as a function of angle, according to some embodiments of the present disclosure.
Figure 6C:
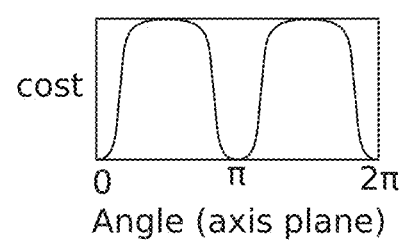

Reference is now made to FIG. 6A, which schematically illustrates non-linear effects of angle changes on foreshortening effects, according to some embodiments of the present disclosure. Reference is also made to FIGS. 6B-6C, which schematically illustrate non-linear cost functions as a function of angle, according to some embodiments of the present disclosure.

As the example of FIGS. 5A-5D illustrates, competing conditions may impose conflicting criteria on the choice of an image angle for a target region 3. Furthermore, there may be more than one target region 3 (methods of managing this are discussed, for example, in relation to FIGS. 11A-11C). Even if a target region 3 is the only primary target, there may be secondary criteria for evaluating an image viewing angle such as whether there are vascular crossings in the image even at positions away from target region 3. A procedure allowing joint evaluation of all these criteria may be described as implementing a cost function for each evaluated angle. Herein, a cost function is discussed in terms of a "higher score" resulting in a reduced fitness of a potential viewing angle. However, the converse formulation of a value function may also be used in some embodiments of the invention.

One consideration in a cost function is that not every angular offset from a nominally preferred ("candidate") viewing angle is necessarily equally costly in terms of impact on the image results. Furthermore, angular increments at small angles have potentially less impact on the image results than angular increments at large angles.

In illustration of the second point, FIG. 6A represents a smaller angle 403 and a larger angle 401, which is twice as large as angle 403. However, the perceived foreshortening 401A for the larger angle 401, as seen from a viewing angle 402, can be considerably more than twice as large as the perceived foreshortening 403A for the smaller angle 403. This variation (which follows the value of the cosine function, with the direction of ray 15 being considered as the 0° angle) can become a significant consideration when considering competing viewing angle options, each of which may improve a result with respect to some criteria (reduce their cost), while increasing cost with respect to other criteria.

For example, foreshortening as a fraction of total target length is relatively unimportant for imaging angles which are a small amount off-perpendicular (e.g., a 5° difference potentially yields <0.5% foreshortening), increasing non-linearly as the imaging angle falls increasingly off the perpendicular direction (e.g., about 3.5% for a 15° difference, and about 13% for a 30° difference).

In some embodiments, foreshortening cost of an imaging angle is given by Equation (2):

$$1-\cos(\Theta-\Phi) \qquad (2)$$

Where $\Theta$ corresponds to a potentially non-perpendicular viewing angle of a target region 3, and $\Phi$ is the angle perpendicular to the target region 3. With a plurality of target regions (for example as described in relation to FIGS.

10A-11C), the foreshortening weighting can be per target region j, optionally weighted by $K_j$, as shown below in Equation (3), $$\Sigma_j K_j(1-\cos(\Sigma_j - \Phi_j)) \quad (3)$$

Optionally, $\Theta_j$ is treated as a constant for all target regions j, i.e., as if the imaging is performed from infinity, although it may be allowed to vary according to position in the image and the size of the field of view.

Another example of foreshortening cost is a threshold, where angular offsets from perpendicular of less than some cutoff value (e.g., causing <1% foreshortening) are considered to impose no cost.

The cost function can deviate from a sinusoid, and may be different for different angular axes.

In FIG. 5D, only rotations of the viewing angle along plane 5 perpendicular to the target region 3 were considered. However, small changes of viewing angle outside of that plane are potentially relatively inexpensive. In some cases, a larger change along the plane 5 (e.g., to avoid an overlap condition) can be replaced without significant degradation of the result (and potentially with an improved result) by making a smaller change along the plane 5 and a small change offsetting the viewing angle from the plane 5, or potentially just a small change offsetting the viewing angle from the plane 5.

FIGS. 6B and 6C illustrate different cost functions for different viewing angle axes, defined relative to the structure of target region 3. Each is similar to a distorted sinusoid in the examples shown. FIG. 6B illustrates a relatively permissive cost function for viewing angles within axially perpendicular plane 5. It becomes maximally expensive close to $$\pm \frac{\pi}{2}$$

(±90°), but for the majority of angles it is closer to the minimal cost. The cost, in this case, optionally represents foreshortening of vasculature that is near the target region 3 (e.g., adjacent vascular branches), which is potentially more acceptable than foreshortening of the target region 3 itself.

FIG. 6C illustrates a less permissive cost function for an axis of viewing angle change, which is in a plane perpendicular to the plane 5 (e.g., in a plane which contains the longitudinal axis of a blood vessel extending through the target region 3). This becomes maximally expensive close to $$\pm \frac{\pi}{2}$$

(±90°), but the cost rises quickly within a fairly small angle change away from 0°, as the amount of foreshortening introduced changes from negligible at small off-angle directions to essentially unusable at medium and greater off-angles.

Figure 7:
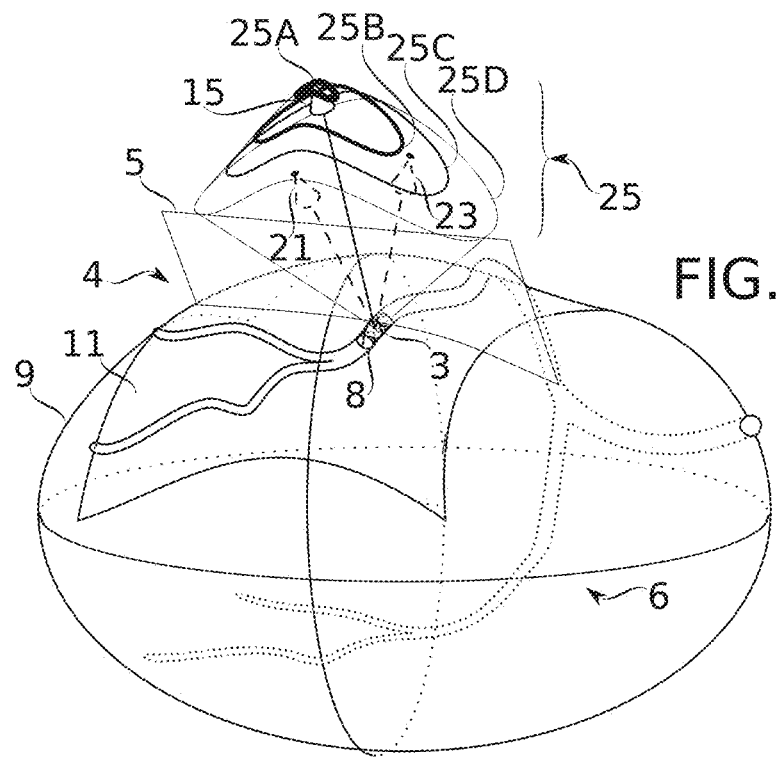
FIG. 7 schematically illustrates a continuously defined cost function for determining a viewing angle, according to some embodiments of the present disclosure.

Reference is now made to FIG. 7, which schematically illustrates a continuously defined cost function 25 for determining a viewing angle, according to some embodiments of the present disclosure.

An example of a cost function 25 which treats two different angular axes differently is schematically indicated in FIG. 7. For purposes of illustration, isocontours 25A, 25B, 25C, 25D represent different cost levels of the cost function 25 and are drawn on the surface of a sphere. Areas inside the isocontour 25A (shown as a bolded line) are "cheapest", and areas at or outside isocontour 25D (shown as thin lines) are the most expensive. Distortion of the isocontours 25A-25D from the shape of a circle is due to viewing angle displacement from surface-perpendicular candidate ray 15 being "cheaper" along an angular axis defined by plane 5, and more expensive on an angular axis perpendicular to the plane 5. The cost functions used for the two angular axes may be like those of FIGS. 6B-6C; or other cost functions may be used for example, ramps, thresholds, and/or other curves.

Absent further constraints, a viewing position looking back along original candidate ray 15 (or, equivalently, along its reflection) provides the uniquely optimal viewing angle.

Values of the cost function at angles with non-minimal cost come into play when further constraints are added, examples of which are next described in conjunction with FIG. 7 and FIGS. 8-11C.

In some embodiments, a limited set of possible viewing angles are available, for example, viewing angles from positions back along ray 21 and ray 23. This may be, for example, because a selection is to be made from already existing images, which were not necessarily taken from angles optimal for the currently selected target region 3.

The example cost function 25 enables viewing angles back along rays 21, 23 to be readily distinguished from one another in cost, even though they may be both equally close to candidate ray 15 in absolute angular difference. Ray 23 is within isocontour 25C, making it "cheaper" in terms of cost function 25 than ray 21, which falls beyond isocontour 25C.

Figure 11A:
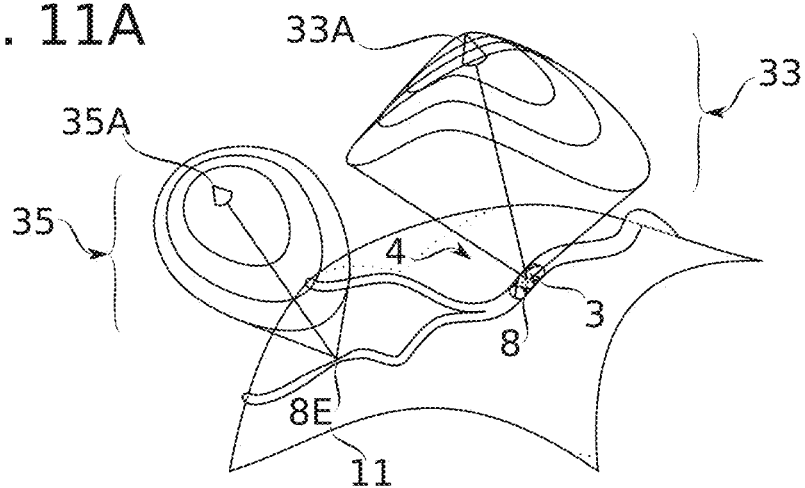
FIGS. 11A-11C schematically illustrates joint use of separately calculated cost functions, according to some embodiments of the present disclosure.
Figure 11B:
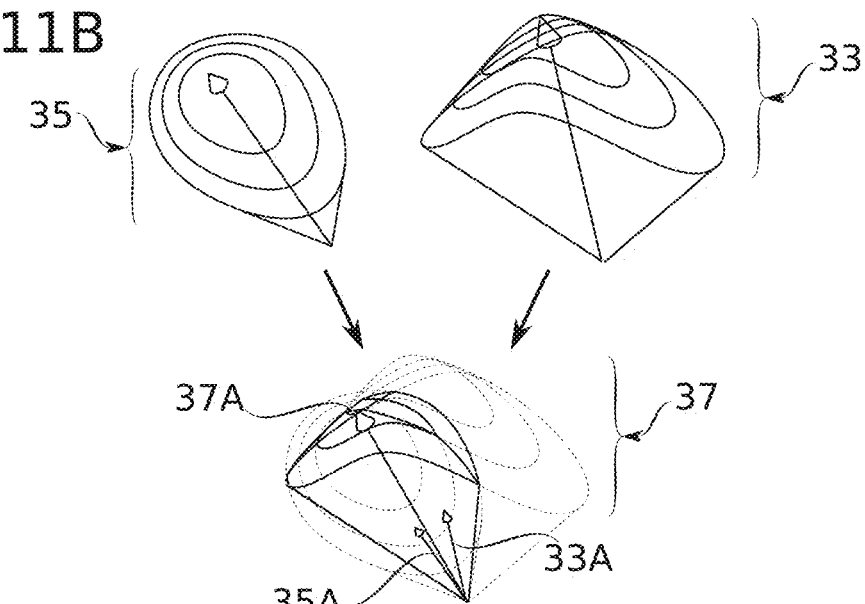
Figure 11C:
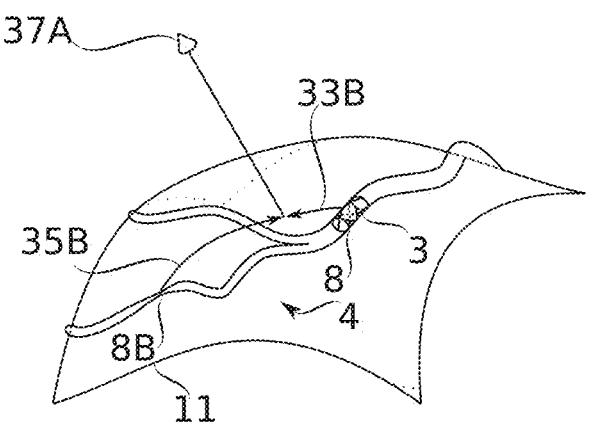

The schematic cost function 35 (as well as other cost functions such as cost functions 33, 35, 37 of FIGS. 11A-11C) are shown herein as if calculated for a relatively restricted range of angles around a center ray; e.g., as if the cost of viewing angles outside this range is effectively maximum. However, cost functions optionally extend to any suitable range of angle space, including a spherical 360°. For 3D imaging methods like X-ray imaging, the cost functions may generally be symmetrical about a plane dividing the cost function space into hemispheres (whether or not the cost function is calculated for the whole hemisphere), since the view from either hemisphere is substantially the same, apart from reflection.

For purposes of selecting from an already obtained image, it should be noted that cost function 25, and any of the other cost functions herein described, is optionally combined with costs associated with image cost factors other than viewing angle. For example, there may be a plurality of images available of a contrast injection event, from different angles. An associated "contrast" cost function is optionally provided which is highest before contrast agent injection, decreases during the seconds following the contrast agent injection, and increases again as contrast agent washes out. Given two of the plurality of images, each taken at a different viewing angles, a relative weighting of the contrast cost function and the foreshortening cost function may be set so that a slight difference in preferred viewing angle does not overwhelm the choice of an image from a period of good contrast agent distribution.

In some embodiments, information of interest (e.g., locations that receive dye filling) is distributed over a plurality of frames. The frames, which can be readily combined (e.g., superimposed and/or viewed sequentially in a cineangiogram), may be taken from the same angle or acceptably similar angles; and/or with the same heartbeat phase or acceptably similar heartbeat phases. In some embodiments, how an image relates to other images in terms of these parameters is optionally used as a part of the weighting, to help a cost function for an image. An image which is part of a more complete cineangiogram, for example, may be weighted as incurring lest cost.

Optionally, cost function evaluation is performed jointly for a set of images that are to be viewed in some combination. For example, inter-image differences in phase and/or angle are weighted in evaluating which images are combined in a cineangiogram producing an optimal available view, e.g., of an event such as a dye injection. For example, a cost function for phase may rank phase angle differences as more costly during high-motion portions of the heartbeat cycle, and less costly (for the same phase angle difference) during low-motion portions of the heartbeat cycle. Optionally, viewing angle differences are also weighted (e.g., non-linearly, for example, with a non-linear sinusoidal increase with increasing angular difference) as part of an evaluation of which images potentially "go together" in a single cineangiogram or other image combination. Optionally, the cineangiogram is optimized for a stable viewing angle. Optionally, the cineangiogram is allowed to show some "rotation" of the viewing angle over the course of the cineangiogram. In some embodiments, images with parameter differences (e.g., in viewing angle and/or heartbeat phase) are post-processed to make the images approximately more similar to one another, e.g., subjected to linear and/or non-linear transformations in their shape. Potentially, small angular differences are more amenable to repair by such approaches than large angular differences, e.g., because features moving in different planes as a result of viewing angle rotation experience more similar distortions in the 2-D image when the distortions are smaller.

Additionally or alternatively, the selection of an image may comprise selection of a cineangiogram. A cineangiogram, in some embodiments, is a time sequence of angiographic frames taken at about, for example, 10-15 Hz or another frequency that can, for example, be examined frame-by-frame, and/or displayed as a brief "movie". A cineangiogram potentially allows, for example, selection of a frame from within the cineangiogram showing a stent in a particular state of expansion and/or flexion. A cineangiogram may also enable viewing of dynamics of contrast flow-in, or another time-dependent feature. Use of a cineangiogram for non-contrast imaging is discussed, for example, in relation to FIGS. 13A-13H, herein.

For selecting a cineangiogram, the selection is preferably of an image that is part of a sequence of images (e.g., at least 4, 6, 8, 10 or more images) obtained from substantially the same viewing angle. The "best viewing angle" image available might be part of a shorter sequence of images obtained at a slightly worse viewing angle. In some embodiments, a criterion relating to how many images are in the cineangiogram sequence that a certain image is a part of is weighed together, with one or more viewing angle criteria such as foreshortening and/or overlap avoidance (and optionally also other criteria such as the contrast cost function just described), to obtain an image that jointly satisfies a plurality of viewing angle and optionally non-viewing angle criteria without any single criterion necessarily dominating the others.

Figure 8:
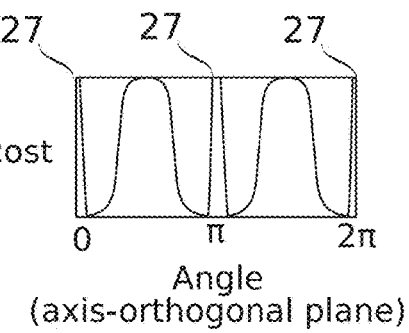
FIG. 8 schematically illustrates a cost function for an angular axis, which includes a cost peak corresponding to positions of overlap that tend to obscure a view of a target region, according to some embodiments of the present disclosure.

Reference is now made to FIG. 8, which schematically illustrates a cost function for an angular axis that includes a cost peak 27 corresponding to positions of overlap tending to obscure a view of a target region 3, according to some embodiments of the present disclosure. The example cost peak 27 indicates, for example, a viewing angle producing overlap, for example as described in relation to FIGS. 5A-5F.

Reference is now made to FIG. 9A, which schematically illustrate effects on a two-angular axis cost function 29 due to overlap of a target region 3 by an interfering region 19, and selection of an image according to its viewing angle and the overlap-adjusted cost function 29, according to some embodiments of the present disclosure.

The example cost function 29 may be understood as a (schematic) 2-angular axis cost function incorporating a portion of the single-axis cost function of FIG. 8, including cost peak 27. Isocontour 29A (thickest contour) represents the cost function minima, with angles closer to the angle of ray 15 having increased cost due to overlap of the target region 3 with the interfering vascular region 19). Additionally, angles (e.g., isocontours 29B, 29C) that are further from the angle of ray 15 have an increased cost due to increased angular distance from the ray 15, which would be preferred (apart from overlap) because it is estimated to be orthogonal to the features at (and surrounding) the target region 3. It is noted that in an actual (non-schematic) cost function, the "hole" in the cost function 29 would most likely extend to the edges of the calculated region shown, reflecting the fuller extent of the blood vessel comprising region 19, and the angular region that it potentially "contaminates".

Rays 21 and 24 represent rays back along a path that correspond to respective viewing angles of two existing images. Although in this instance, ray 24 is angularly closer to candidate ray 15, the ray 21 corresponds to the preferred viewing angle, because it occupies a region away from overlap. This is the case even though it introduces a slight foreshortening of the target region 3 and the structure 8 (which may be a stent selected for measurement). In effect, the cost function is constructed to enable selecting between the non-optimal conditions of an image showing a foreshortened target region 3, and an image showing an obscured target region 3.

Reference is now made to FIG. 9B, which schematically illustrate effects on a two-angular axis cost function 29 due to overlap of a target region 3 by an interfering region 19, and selection of an image according to its viewing angle and the overlap-adjusted cost function 29, according to some embodiments of the present disclosure.

When preparing to record an angiographic image, generally almost any angle can be selected, without limitation to a small number of discrete choices. In that case, the optimum angle can be chosen as substantially any viewing angle falling on isocontour 29A; for example, a viewing angle looking back along ray 31.

It is noted in particular that isocontour 29A is optionally constructed with respect to optimizing the viewing of a target region 3 and/or a structure 8 within it. Foreshortening costs may be calculated, for example, with respect to the particular extended-cylinder shape and orientation of the target region 3. This prevents, e.g., the case where a global optimization of foreshortening results in a sub-optimal representation of the focus of a procedure and/or measurement.

Similarly, overlaps in the image are optionally prevented specifically in the neighborhood off the target region 3. A global optimization minimizing overlap (or another optimization that does not give special weight to the outcome near the target region 3) could result in a case where the overlap that remains after optimization is still in the wrong place.

Figure 10A:
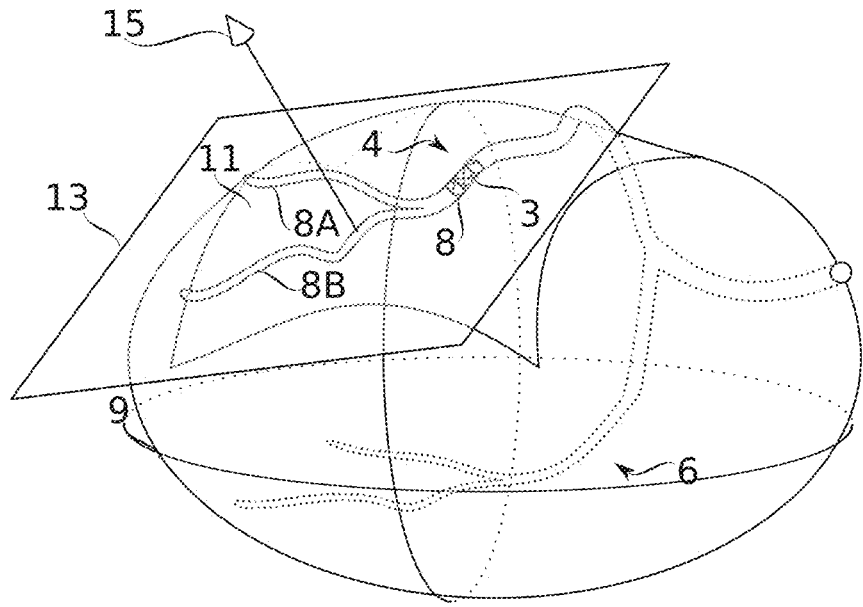
FIGS. 10A-10B schematically illustrate examples of target regions, which include regions outside a single blood vessel segment region, according to some embodiments of the present disclosure.
Figure 10B:
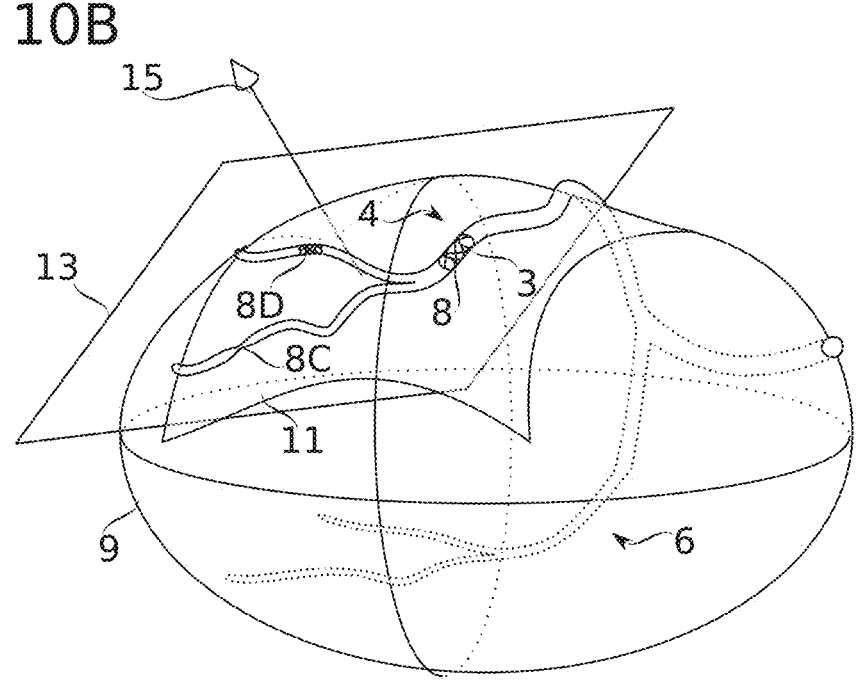

Reference is now made to FIGS. 10A-10B, which schematically illustrate examples of target regions that include regions outside a single blood vessel segment region, according to some embodiments of the present disclosure.

In some embodiments, an image to be recorded of a target region 3 is jointly optimized for analysis and/or examination of selected further structures, for example, downstream vascular branches 8A, 8B (FIG. 10A), or other discrete structures such as regions comprising another stenosis 8C and/or stent 8D (FIG. 10B). In some embodiments, the further structures (e.g., downstream vascular branches) are selected by the position of a lesion; e.g., they are targeted because the lesion is positioned to affect specifically those downstream branches.

In some embodiments, a target region may be associated generally with the whole extent of the plurality of features targeted, e.g., resulting in a surface perpendicular direction 15 arrived at as a weighted sum of the orientations of all blood vessels within the region (FIG. 10A) and/or all individual targets of interest (FIG. 10B). Optionally, some blood vessels and/or features are weighted more than others. For example, the target region 3 may be assigned extra weight to help keep foreshortening of this vascular portion in particular potentially minimized.

In some embodiments, criteria weighting is varied for different regions according to the criterion. For example, minimization of foreshortening is optionally of primary concern for a target region 3, so that the "foreshortening" contribution cost function is calculated based just on the target region 3, or with the target region 3 being weighted higher than other contributing regions (e.g., vascular branches 8A, 8B, stenosis 8C, and/or stent 8D). For the overlap contribution to the cost function, overlaps are optionally weighted more equally for each of (for example) the target region 3, the vascular branches 8A, 8B, the stenosis 8C, and/or the stent 8D.

In some embodiments (e.g., at a standard magnification suited to fitting a whole target organ in the view in one image), the center of imaging is chosen so that all of the vasculature 2 is in-frame. The center of imaging is not necessarily centered on the target region 3, nor it is to necessarily adjusted for an expanded range of features. It is noted, however, that by selecting a viewing angle which is near to perpendicular to the surface of shell 9 in the vicinity of the target region 3, centering an organ which generally conforms to the shape of shell 9 in the view typically results in approximately centering the target region 3 in the view.

Nevertheless, it should be noted that the center point of the imaging is optionally shifted to different positions as well. For example, the center point may be shifted in cases where magnification prevents obtaining the whole of a vasculature 2 in a frame. The center point may also be shifted to compensate for shifts in the image position of a target feature 3 due to changes in viewing angle away from perpendicular to the shell 9 and/or the general arrangement of vascular features in the vicinity of target region 3.

Optionally, cost functions are generated for magnification and/or centering, as applicable. These cost functions may also be subject to differences depending on the role of a particular feature in the image to be obtained. For example, imaging parameters may be penalized for imaging one or more regions j away from the center of an image $A_{center}$, as shown below in Equation (4)

$$K_j K_j d(j, A_{center}) \quad (4)$$

The weighting function may be defined as $K_j > 0$ just for a subset of all features j, and otherwise as $K_j = 0$.

Additionally or alternatively, features (potentially less important features) may be associated with a penalty for being out-of-frame (feature j outside of image A), as shown below in Equation (5):

$$\sum_j \begin{array}{ll} 0: & \text{if } j \text{ in } A \\ 1: & \text{if } j \text{ not in } A \end{array} \quad (5)$$

Reference is now made to FIGS. 11A-11C, which schematically illustrate joint use of separately calculated cost functions 33, 35, according to some embodiments of the present disclosure.

In some embodiments, a plurality of viewing angle cost functions (e.g., cost functions 33, 35) are constructed for a plurality of different regions and evaluated jointly. For example, cost function 33 penalizes rotations along one angular axis differently than a perpendicular axis, while cost function 35 imposes similarly differential penalties—but for two different angular axes, chosen with respect to the local vascular orientation at secondary target region 8E. It should be noted that (for example, in the presence of a plurality of generally cylindrical target regions 3, 8E) the cost function for changes of the angular axis within the plane of no foreshortening perpendicular to the longitudinal axis of each cylinder, the foreshortening penalty can optionally be set fully to 0. The presence of other features, with different orientations, potentially provides a natural constraint on this angular axis that helps maintain the overall area in which features of interest lie oriented to face the viewing angle.

In some embodiments, geometric features of the 3-D model are used in selecting the extent and/or importance (relative weighting) of features included in the cost function calculation. For example, the extent of a lesion used in generating a cost function optionally depends on the length of a region of lesioning (e.g., stenosis), and/or diffusion of the lesion among a plurality of branches, with stenotic areas identified sufficiently near one another being optionally joined into a single lesion, depending on whether their nearness remains under a threshold criterion for maximum distance, or another criterion.

In some embodiments, lesions are assigned weights for their importance in selecting an image viewing angle minimized for minimum foreshortening and/or overlap based on one or more of their overall extent, severity (e.g., percent constriction), or another feature. In some embodiments, a functional and/or anatomical measure is used as a weighting criterion to determine which vascular portions are more relatively important to display with reduced foreshortening and/or overlap. Use of a calculated fractional flow reserve (FFR) value to select vascular features of interest is described, for example, in conjunction with FIGS. 12A-12F.

FIG. 11B schematically illustrates combining a plurality of cost functions 33, 35. The resulting cost function 37 represents the (optionally weighted) sum of the cost functions, e.g., with ray 37A indicating the angle of minimum mutual cost, potentially different than either of rays 33A, 35A. In the particular example, the cost functions are optionally added with equal weighting. However, the cost functions can be combined with different weightings, and/or an operator different than simple addition. For example, the cost functions may be combined based on a Euclidean distance operator, where each cost function penalty is treated as a component of a vector in a "penalty space" of two or more dimensions.

FIG. 11C shows ray 37A with respect to vascular neighborhood 4. This is optionally the ray back along which the optimal viewing angle points. Optionally, the effective center of the image frame is also changed, e.g., as a result of the rotation of the viewing angle. Optionally, translation centering is further adjusted (for example as described in relation to block 508), e.g., to jointly optimize centering of features of interest in the frame.

Examples of Vascular Models and/or Images

Figure 12A:
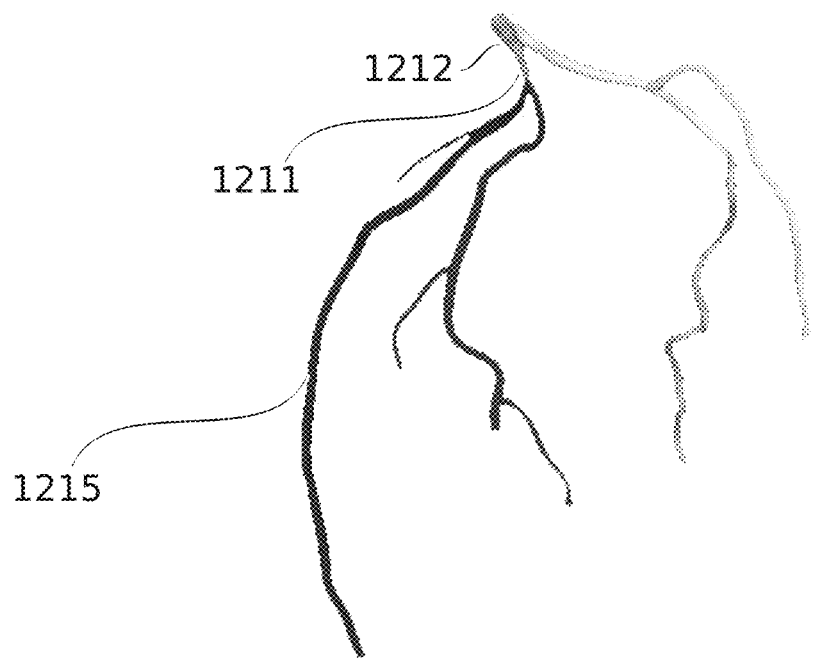
FIGS. 12A-12B schematically illustrate a vasculature model and corresponding 3-D angiogram, according to some embodiments of the present disclosure.
Figure 12B:
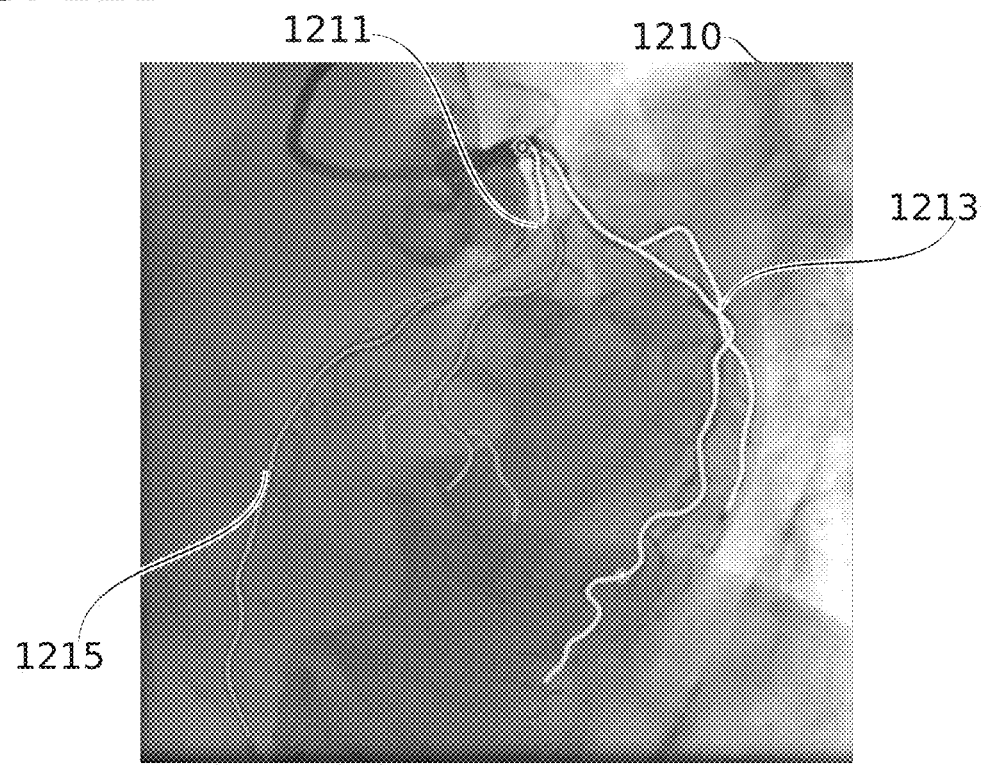
Figure 12C:
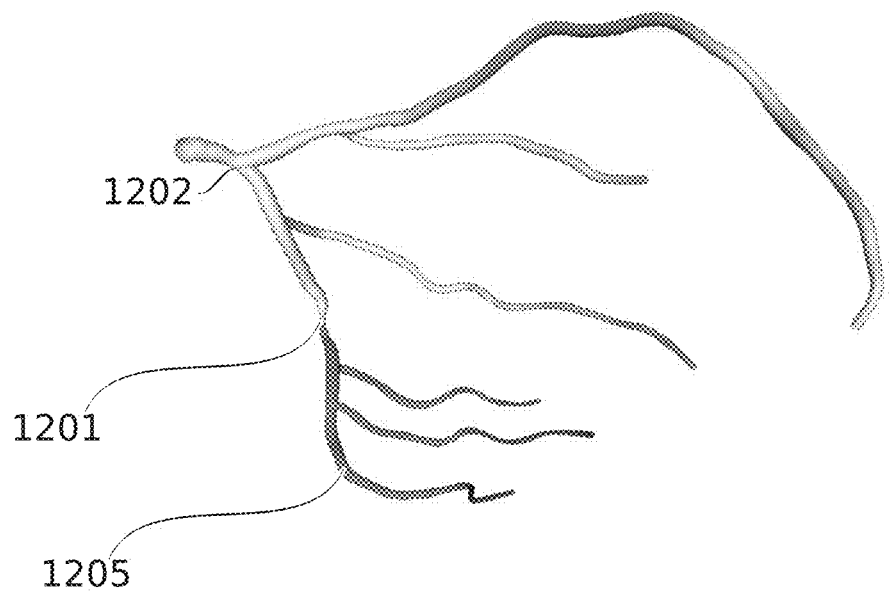
FIGS. 12C-12D schematically illustrate a vasculature model and corresponding 3-D angiogram, according to some embodiments of the present disclosure.
Figure 12D:
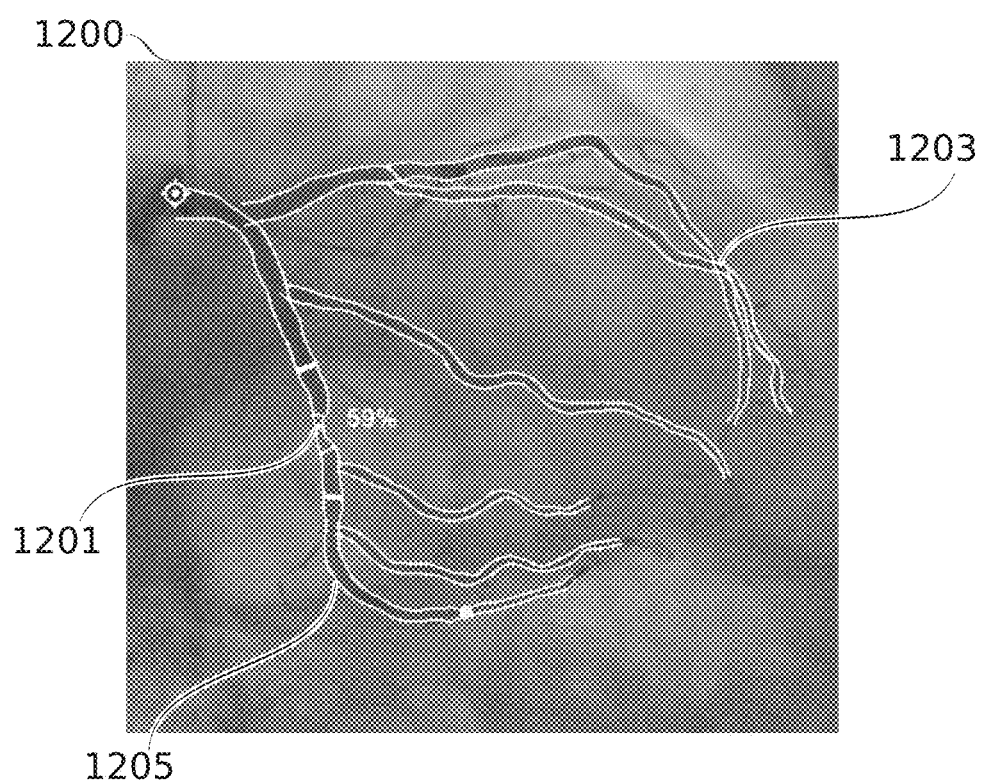
Figure 12E:
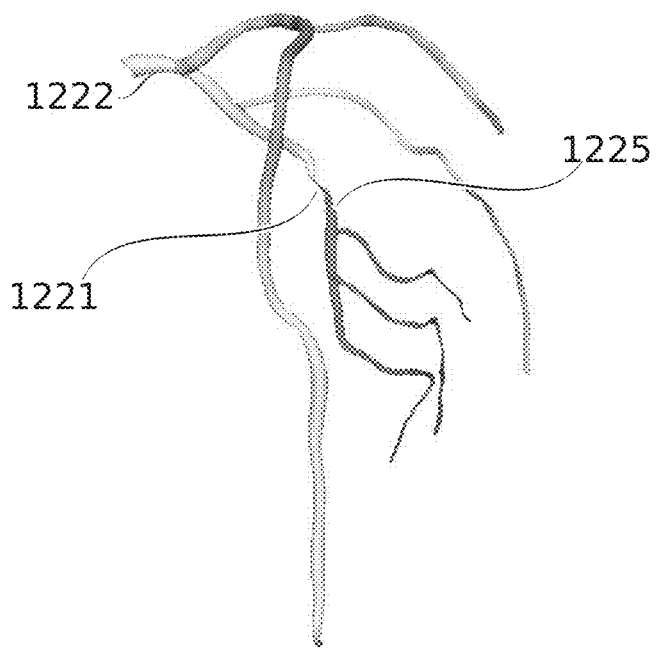
FIGS. 12E-12F schematically illustrate a vasculature model and corresponding 3-D angiogram, according to some embodiments of the present disclosure.

Reference is now made to FIGS. 12A-12B, which schematically illustrate a vasculature model 1212 and corresponding 2-D angiogram 1210, according to some embodiments of the present disclosure. Reference is also made to FIGS. 12C-12D, which schematically illustrate a vasculature model 1202 and corresponding 2-D angiogram 1200, according to some embodiments of the present disclosure. Further reference is made to FIGS. 12E-12F, which schematically illustrate a vasculature model 1222 and corresponding 2-D angiogram 1220, according to some embodiments of the present disclosure.

The angiograms 1200, 1210, 1220 were obtained using X-ray imaging after contrast injection to the coronary arteries. The blood vessels shown are arteries surrounding the chambers of the heart of a human patient. Blood vessels corresponding to the blood vessels of vasculature models 1202, 1212, 1222 are indicated by lines traced over the images.

Vascular models 1212 (FIG. 12A), 1202 (FIG. 12C), and 1222 (FIG. 12E) illustrate (each from a selected point of view) a 3-D vascular model which has been shaded to represent relative blood flow function. Flow function is optionally calculated, for example, as a fractional flow reserve (FFR) estimate, which may be based on vascular geometry, and/or other criteria; for example as described in one or more of International Patent Publication No. WO2014/111930, International Patent Publication No. WO2014/111927, and International Patent Publication No. WO2014/111929; the contents of which are hereby included herein by reference in their entirety.

In the model figures, darker shading corresponds to more reduced blood flow function. A similar convention using different shades is used in the lines drawn over angiogram 1210. Blood vessels with blood flow include arteries 1215, 1205, 1223, and 1225, which are respectively downstream of stenoses 1211, 1201, and 1221. In angiogram 1200, flow function at stenosis 1201 is shown at an estimated 59% of normal flow for an unstenosed blood vessel. In angiogram 1220, flow function at stenosis 1221 is shown at an estimated 73% of normal flow for an unstenosed blood vessel. Stenoses 1211, 1201, 1221 are likely targets for revascularization treatment, such as by implantation of a stent.

The viewing angles of the models are potentially "optimal", in the sense that the blood vessel portions comprising the stenoses 1211, 1201, 1221 are oriented substantially perpendicular to the viewing angle, apparent crossing of modeled blood vessels is minimized (there are no crossings in models 1212 and 1202), and the other blood vessels also are spread across a wide extent of the overall imaging area (consistent with a minimization of foreshortening for many areas of the modeled vasculature). In particular, blood vessels which are darker (lower FFR, and considered to be more diseased) are shown in orientations so that they are among the blood vessels which receive the least foreshortening. This result is obtained, in some embodiments, by using FFR value in constructing a cost function, so that foreshortening and/or overlap of vascular regions with a low FFR value is penalized more than other regions.

In a case where a new image is to be recorded, the viewing angle shown is optionally among the viewing angles which are optimal (e.g., have the lowest cost functions/highest quality score). The shown viewing angle (optionally together with its reflection) is potentially the sole optimal angle.

In a case where an image is to be selected from among images that already have been obtained, the precise viewing angles shown in the figures may be unavailable. In some embodiments, an image that has the best angle quality score is used.

An application that uses, in some embodiments, selection of a single image (whether new or previously obtained) comprises updating a model and/or updating a parameter calculated from the model using that single image. Optionally two or more images are selected and used in the updating. The single-image case is described as an example of the more general case of at least one image, e.g., one, two, three, or more images.

For example, International Patent Publication No. WO2015/059706, the contents of which are hereby included herein by reference in their entirety, describes recalculation of a functional parameter such as FFR, optionally from a single 2-D image region. FFR calculation potentially depends on the different resistances to flow within a multi-segment crown of blood vessels. The recalculation is simplified, in some embodiments, by a vascular segment resistance that is re-calculated from a single 2-D image region having coarse homology to a region of the model it replaces, augments, combines with, and/or is compared. Methods of the current application are optionally used for selecting this single 2-D image (or images, or suitable region(s) thereof). The selection is potentially used in streamlining (e.g., enhancing automation of) the process of post-stent evaluation. In some embodiments, for example, FFR is recalculated using a single image for a purpose such as verification of the implantation of a stent and/or its effects on improving blood flow. This potentially bypasses a requirement to regenerate a full 3-D reconstruction after change in a local region of the vasculature. Optionally, even a partial 3-D reconstruction of the changed region itself is avoided.

For example, the 2-D X-ray angiogram 1210 of FIG. 12B and 2-D X-ray angiogram 1200 of FIG. 12D are images of the same vasculature modeled respectively by vascular models 1212, 1202. Optionally, the angiograms are among angiograms from which the vascular models 1212, 1202 were generated, for example using one or more of the methods described in International Patent Publication No. WO2014/111930, International Patent Publication No. WO2014/111927, International Patent Publication No. WO2014/111929, and International Patent Publication No. WO2015/059706, the contents of which are included herein by reference in their entirety. The viewing angle of angiograms 1210, 1200 are potentially less optimal than that the viewing angle used in rendering models 1212, 1202, since each contains a blood vessel crossing 1213, 1203. However, these crossings are each relatively far away from (e.g., and in particular, not downstream of) stenoses 1211, 1201. Accordingly, the blood vessel crossings 1213, 1203 would be accorded a relatively low penalty, and accordingly would have an improved chance of being selected from among a set of images as one which most clearly shows targets 1211 1201 and its downstream vessels (e.g., including artery 1215, 1205).

Figure 12F:
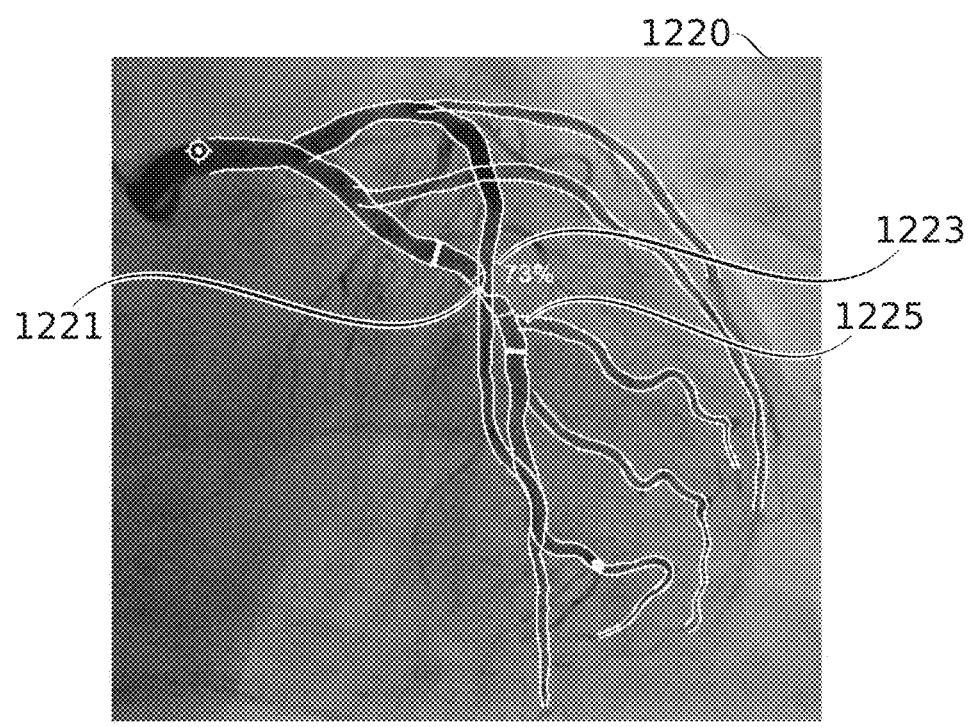
Figure 13A:
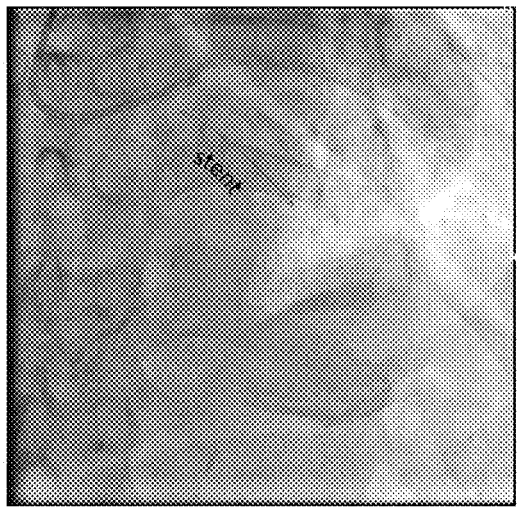
FIGS. 13A-13H show examples of 3-D angiographic images obtained with and without contrast agent, according to some embodiments of the present disclosure.
Figure 13B:
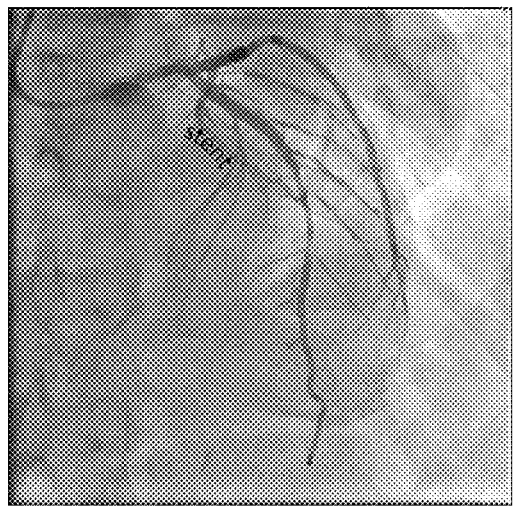
Figure 13C:
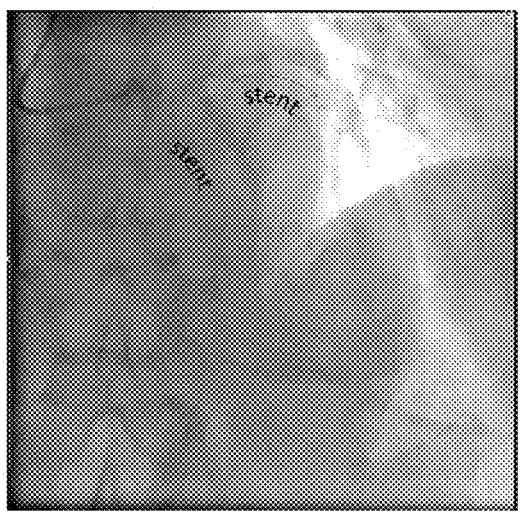
Figure 13D:
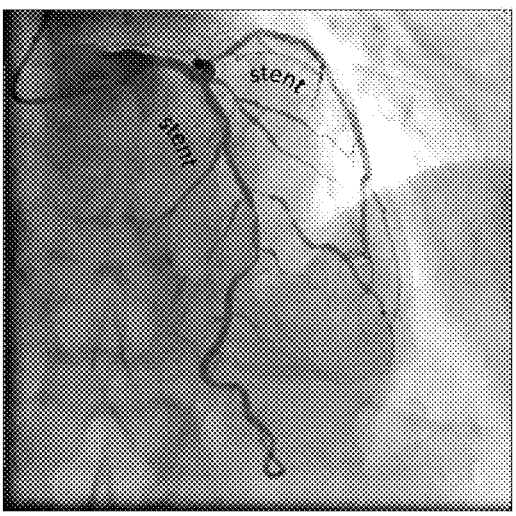
Figure 13E:
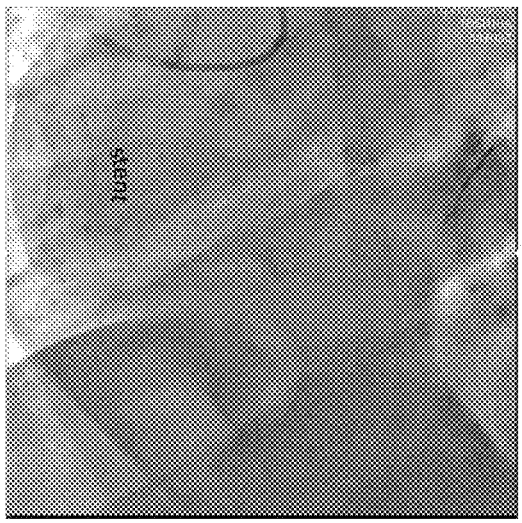
Figure 13F:
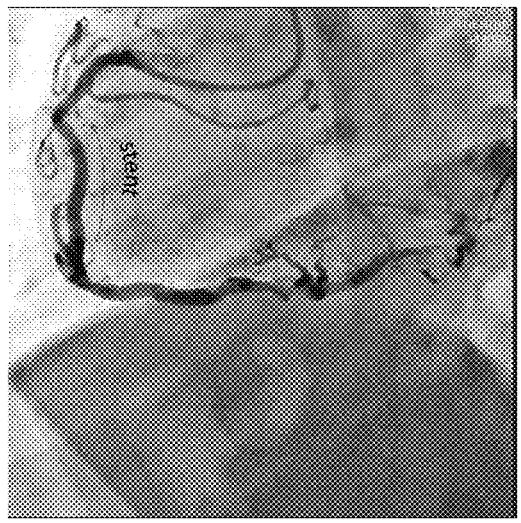
Figure 13G:
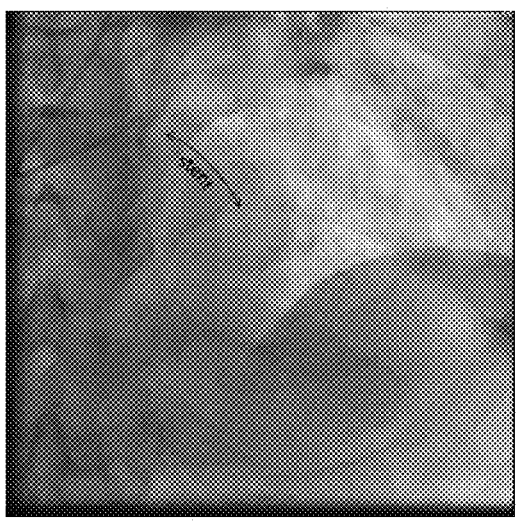
Figure 13H:
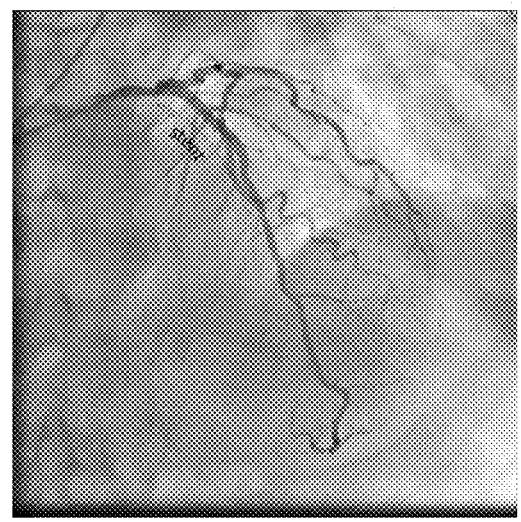

The 2-D X-ray angiogram 1220 of FIG. 12F is an example of an image taken from an angle which would potentially be rejected, in some embodiments of the disclosure. Arteries 1223 and 1225 overlap within the region of stenosis 1223, which is the likely target of treatment. By appropriate adjustment of the viewing angle (for example to the orientation of model 1222), the majority of this interfering effect can be removed, while also keeping foreshortening minimal.

Reference is now made to FIGS. 13A-13H, which show examples of 2-D angiographic images obtained with and without contrast agent, according to some embodiments of the present disclosure.

In some embodiments, an angiographic image and/or cineangiogram is obtained without contrast injection. Although the contrast of blood vessels is much lower without contrast injection ("contrast-free" imaging), an implanted stent may be discernible within a contrast-free angiographic image; for example, based on its inherent radiopacity and/or radiopaque markers.

The plurality of images in a contrast-free cineangiogram can also provide a potential advantage by making the stent more obvious by its movements as the heartbeats. Optionally, a cineangiogram provides images which cover enough of the range of the stent's movements during a heartbeat cycle that moments during the heartbeat cycle with the stent in its (for example) most expanded diameter can be reliably selected. This potentially assists in making accurate estimates of the degree of flow capacity restored by a stent.

For a human observer to readily distinguish the potentially faintly visible stent against its background, it is a potential advantage to show the stent in a predictable location (optionally centered, and/or in a location that can be indicated relative to landmarks from another image) and/or orientation (e.g. with minimal foreshortening).

In some embodiments of the disclosure, the viewing angle of an existing image is selected for selection of the viewing angle of a new image and/or cineangiogram. The existing image optionally is a contrast image (e.g., taken pre-implantation of a stent), which shows the location (or eventual location) of the stent clearly enough that it serves as a ready reference. While in principle the new image can be taken from any viewing angle available to the instrument (e.g., medical imaging device), it is a potential advantage for the viewing angle to be identical or similar to the viewing angle used to take the reference image. Optionally, the settings for the new image are presented to a user explicitly in terms of direct device settings (e.g., position angles). Optionally or additionally, settings for the new image are presented to the user as choices related to the existing image (e.g., "image from the angle of this image", where this image may be displayed and/or indicated by a name and/or properties). Optionally, settings for a new image are selected and used to control an imaging device directly and automatically, optionally with an opportunity for a user to override and/or indicate acceptance.

In some embodiments, the viewing angle of a selected existing image that best minimizes the cost criteria of some viewing angle cost function (for example as described in relation to any of the embodiments herein) is used as the imaging setting for the new image and/or cineangiogram. For example, the method of FIG. 1A is performed, and then the viewing angle of the resulting image is also provided as an image setting.

Optionally, the viewing angle of the selected existing image (original viewing angle) is not used exactly for the new image and/or cineangiogram. Instead, in some embodiments, further processing is used to weight the relative costs of angular deviation from the original viewing angle, and angular change that will bring a stent (or other structure 8 of a target region 3) into a more easily identified and/or measured position. For example, an angular cost function based on foreshortening is weighted together with an angular cost function based on how useful a certain reference image is if deviated by, e.g., 5°, 10°, 20°, or another angle. This may be understood as an embodiment that uses the result of block 116 of FIG. 1A as an input into block 122 of FIG. 1B.

It should be noted that within some angular limits, a non-isometric distortion of the reference image can be used, in some embodiments, to approximate it more closely to the view of the imaged structure 8. Conversely, the new image may be distorted to enable a target to be located, or both images may be partially distorted to approximate a view from a viewing angle intermediate to both of the images.

In some embodiments, the extent of a stent and/or region designated to receive a stent defines a portion of target region 3. FIGS. 13A, 13C, 13E, and 13G each show an angiogram of an area including a stent, and FIGS. 13B, 13D, 13F and 13H each show corresponding angiograms of the same areas, respectively, during injection of contrast agent.

It is noted that slight bending in a stented blood vessel is normal, so that it has no single cylindrical axis, except as optionally estimated by an approximation. The bending can be in three dimensions (e.g., curving to follow a surface of the heart as well as curving along the surface). In some embodiments, a corresponding cost function component for foreshortening is optionally based on a single approximate feature-defined axis (e.g., longitudinal axis of a cylindrical approximation of the stented blood vessel) or plane (e.g., best-fit plane). Optionally, the cost function component is calculated for multiple segment orientations of the stented blood vessel, considered jointly (e.g., in an optionally weighted sum).

System Implementing Viewing Angle Selection

Figure 14:
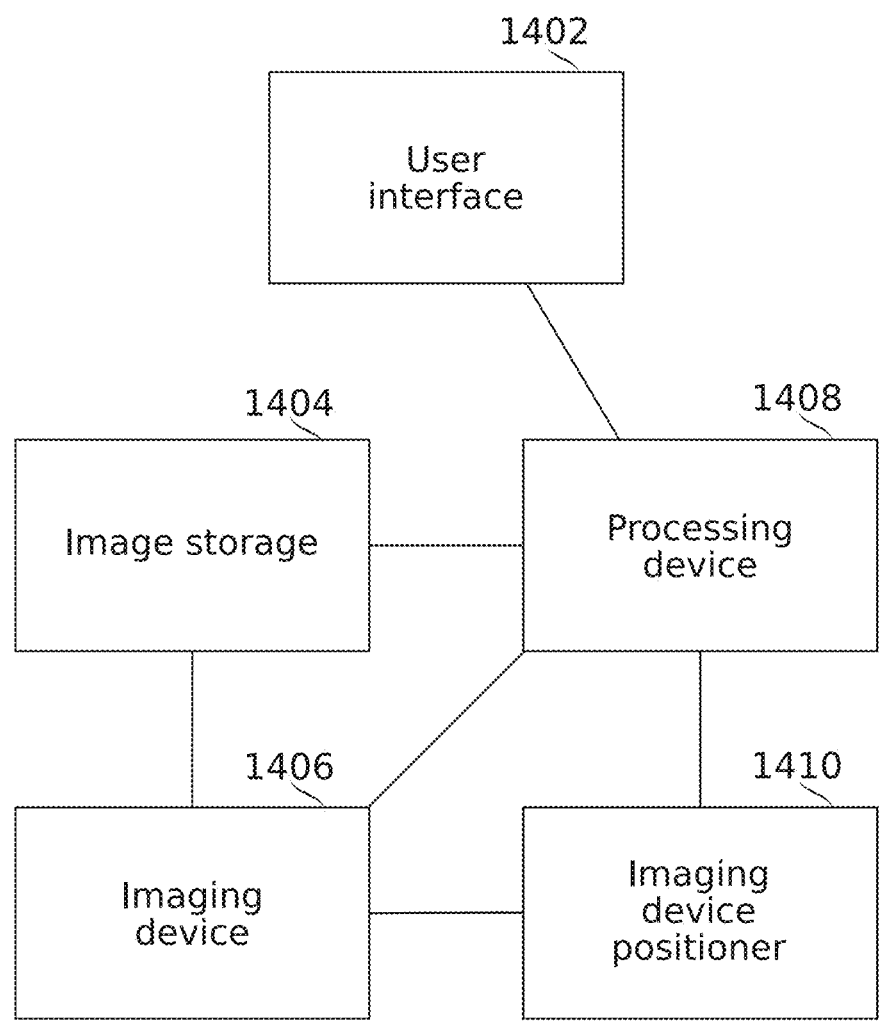
FIG. 14 schematically illustrates a system configured to implement viewing angle selection, according to some embodiments of the present disclosure.

Reference is now made to FIG. 14, which schematically illustrates a system configured to implement viewing angle selection, according to some embodiments of the present disclosure.

Computer processing device 1408, in some embodiments, comprises one or more computational devices configured by programming to implement embodiments of the current disclosure; for example any one or more of the viewing angle selection embodiments described in relation to any one or more of FIGS. 1A-13H.

The processing device 1408 is implemented, e.g., as a stand-alone computer, a computer server, a computerized server-client system, or any other suitable constellation of sub-devices providing, in aggregate, device connections and functionalities further described in this figure.

It should be understood a block of this diagram is optional for any particular set of operations described insofar as that set of operations does not require use of its particular functions. For example, for an operation in which the processing device 1408 automatically sets a viewing angle by operation of the imaging device positioner 1410, user interface 1402 is optional. Nonetheless, the user interface 1402 may be involved in this operation, for example, to confirm an operation before it is automatically carried out, and/or to update the user with new device position information.

User interface 1402, in some embodiments, is functionally connected to the processing device 1408. In some embodiments, the user interface 1402 uses standard computer use interface components comprising screen and input devices such as a pointer controller and/or keyboard. User interface 1402 is configured to do one or more of, e.g.:

Show images to the user, for example, images from viewing angles selected by the processing device 1408.

Present choices to the user (e.g., a options to confirm and/or select from among one or more actions for processing and/or imaging).

Accept choices from the user (e.g., indicating control options to the user and accepting commands such as selections and/or confirmations).

Imaging device 1406, in some embodiments, comprises an imaging device used to capture radiative energy for the formation of angiographic images. In some embodiments, the imaging device 1406 is an X-ray camera. In some embodiments, images from image device 1406 are stored in image storage 1404. In some embodiments, the imaging device 1406 is operable under the control of processing device 1408.

Image storage 1404, in some embodiments, comprises volatile or non-volatile memory holding a data representation of images obtained by the imaging device 1406, obtained by another imaging device during a previous imaging session, and/or generated in whole or in part by image analysis operations performed by the processing device 1408. In some embodiments, the viewing angles of images available in the image storage 1404 define a range of available viewing angles from which a viewing angle is selected by operation of the processing device 1408.

Imaging device positioner 1410, in some embodiments, comprises actuators, armatures, and/or other mechanical devices operable to set a position of the imaging device 1406 to obtain images from a particular viewing angle. In some embodiments, the device positioner 1410 comprises a camera mount that accepts mounting of the imaging device 1406. The mounted imaging device 1406 can be moved (e.g., by swiveling, sliding, or other movements of the imaging device positioner 1410) throughout a range of viewing angles. Optionally, movement of the imaging device position is under the control and/or monitoring of the processing device 1408. In some embodiments, a viewing angle determined and/or selected by processing device 1408 is used to control the imaging device positioner 1410 so that the imaging device 1406 is positioned at the determined and/or selected viewing angle.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A method of selecting an existing angiographic image comprising:
   receiving a plurality of angiographic images;
   receiving a vascular model of a vasculature;
   receiving a selection of a target region of the vascular model;
   determining a viewing angle cost function defining cost function values for a plurality of viewing angles with respect to the target region, the cost function values including a first set of cost function values that are located on a first, lower-cost side of a cost function threshold and a second set of cost function values that are located on a second, higher-cost side of the cost function threshold, wherein the viewing angle cost function penalizes foreshortening due to offsets along a first angular axis defining rotations within a first plane less severely than it penalizes foreshortening due to offsets along a second angular axis defining rotations within a second plane, perpendicular to the first plane;
   selecting an angiographic image from among the plurality of angiographic images, using the viewing angle cost function applied to the vascular model, by identifying an angiographic image that corresponds to a viewing angle having a cost function value that is located on the first, lower-cost side of the cost function threshold; and
   displaying the selected image.

2. The method of claim 1, wherein a set of viewing angles having cost function values that are less distant from the cost function threshold than the cost function value of the viewing angle of the selected image, and on the second, higher-cost side of the cost function threshold, is at least as large as a set of viewing angles on the first, lower-cost side of the cost function threshold.

3. The method of claim 1, wherein a set of angles having cost function values less distant from the cost function threshold than the cost function value of the viewing angle of the selected image, and on the second, higher-cost side of the cost function threshold, is twice as large as a set of angles on the first, lower-cost side of the cost function threshold.

4. The method of claim 1, wherein the viewing angle of the selected image is at a respective local minimum of the viewing angle cost function on the first, lower cost side of the cost function threshold.

5. The method of claim 1, wherein the viewing angle cost function value of the viewing angle of the selected image is within a same value distance from a respective local minimum of the viewing angle cost function, while remaining on the first, lower-cost side of the cost function threshold.

6. The method of claim 1, wherein the viewing angle of the selected image is within a same angular distance from a respective viewing angle having a local minimum of the viewing angle cost function, while remaining on the first, lower-cost side of the cost function threshold.

7. The method of claim 1, further comprising selecting a viewing angle corresponding to a viewing angle of the selected image, and obtaining a new image using the selected viewing angle.

8. The method of claim 7, further comprising selecting an imaging viewing angle within an offset from the viewing angle of the selected image,
   wherein the imaging viewing angle is selected according to a modified cost function that modifies the viewing angle cost function with a cost that increases according to a magnitude of the offset.

9. The method of claim 1, wherein the selecting is also based on a characteristic of a feature shown in the image.

10. The method of claim 9, wherein the feature is a degree of contrast filling of the vasculature modeled by the vascular model.

11. The method of claim 1, wherein the selecting is also based on an availability of further angiographic images that are recorded at a same heartbeat phase as the selected image.

12. The method of claim 1, wherein the selecting is also based on an availability of further images recorded within a certain time period of the selected image.

13. The method of claim 12, wherein the selected image and the further images together comprise a cineangiogram.

14. The method of claim 1, wherein the target region comprises a vascular segment defining a longitudinal axis, and the first plane is perpendicular to the vascular segment.

15. The method of claim 1, wherein a region of the cost function along the first angular axis has values within a range of values of a region of the cost function along the second angular axis.

16. The method of claim 1, wherein the viewing angle cost function is calculated with increased cost for increasing view overlap of the target region with other regions of the vascular model.

17. The method of claim 1, wherein the viewing angle cost function is calculated with decreased cost for viewing angles that show areas of the vascular model with decreased vascular function more clearly.

18. The method of claim 17, wherein decreased vascular function is determined based on a calculated Fractional Flow Reserve (FFR) value for regions of the vascular model.

19. The method of claim 18, wherein showing the areas more clearly comprises one or more of reducing their overlap with structures of the vascular model, and reducing their foreshortening.

20. The method of claim 1, wherein the target region comprises a vascular lesion.

21. The method of claim 20, wherein the vascular lesion is distributed among a plurality of vascular segments separated by a vascular branching point.

22. The method of claim 20, wherein the target region comprises a plurality of vascular branches identified by a position of the vascular lesion.

23. The method of claim 22, wherein the vascular model models an arterial vasculature, and the vascular branches are downstream branches of the vascular lesion.

24. The method of claim 1, wherein the target region comprises a primary target and a secondary target.

25. The method of claim 1, wherein the target region comprises a vascular stent.

26. The method of claim 1, wherein the determining the viewing angle cost function comprises calculating a shell representing a surface across which the vasculature extends.

27. The method of claim 1, wherein the vasculature modeled by the vascular model comprises a portion of a cardiac arterial vasculature.

28. The method of claim 27, further comprising using the selected image, together with the vascular model, to calculate a Fractional Flow Reserve (FFR) of the vasculature.

29. A processor and memory configured to carry out the method of claim 1.

30. The method of claim 1, wherein the viewing angle cost function includes a first weight for foreshortening of the target region and a second weight for overlapping vasculature features with respect to the target region.

31. A method of selecting an existing angiographic image comprising:
- receiving a plurality of angiographic images;
- receiving a vascular model of a vasculature;
- receiving a selection of a target region of the vascular model;
- determining a viewing angle cost function defining cost function values for a plurality of viewing angles with respect to the target region, the cost function values including a first set of cost function values that are located on a first, lower-cost side of a cost function threshold and a second set of cost function values that are located on a second, higher-cost side of the cost function threshold, wherein the viewing angle cost function is determined based on a direction perpendicular to the target region minimizing foreshortening of the target region, and angles offset from the perpendicular direction increasing foreshortening;
- selecting an angiographic image from among the plurality of angiographic images, using the viewing angle cost function applied to the vascular model, by identifying an angiographic image that corresponds to a viewing angle having a cost function value that is located on the first, lower-cost side of the cost function threshold; and
- displaying the selected image.

32. A method of selecting an existing angiographic image comprising:
- receiving a plurality of angiographic images;
- receiving a vascular model of a vasculature;
- receiving a selection of a target region of the vascular model;
- determining a viewing angle cost function defining cost function values for a plurality of viewing angles with respect to the target region, the cost function values including a first set of cost function values that are located on a first, lower-cost side of a cost function threshold and a second set of cost function values that are located on a second, higher-cost side of the cost function threshold,
- wherein determining the viewing angle cost function comprises calculating a shell representing a surface across which the vasculature extends, and wherein the shell comprises a substantially ovate surface;
- selecting an angiographic image from among the plurality of angiographic images, using the viewing angle cost function applied to the vascular model, by identifying an angiographic image that corresponds to a viewing angle having a cost function value that is located on the first, lower-cost side of the cost function threshold; and
- displaying the selected image.

33. The method of claim 32, wherein the ovate surface is defined between portions of the vascular model separated by at least 135° from one another relative to a geometric center of the ovate surface.

\* \* \* \* \*